United States Patent
Baker et al.

(10) Patent No.: US 10,420,764 B2
(45) Date of Patent: Sep. 24, 2019

(54) PHARMACEUTICAL FORMULATION OF N-[5-[2-(3,5-DIMETHOXYPHENYL) ETHYL]-2H-PYRAZOL-3-YL]-4-[(3R,5S)-3,5-DIMETHYLPIPERAZIN-1-YL] BENZAMIDE

(71) Applicant: AstraZeneca AB, Sodertalje (SE)

(72) Inventors: Noel Alan Weldon Baker, Macclesfield (GB); Alpesh Mistry, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/183,088

(22) Filed: Jun. 15, 2016

(65) Prior Publication Data

US 2017/0119759 A1 May 4, 2017

Related U.S. Application Data

(63) Continuation of application No. 14/108,595, filed on Dec. 17, 2013, now abandoned.

(60) Provisional application No. 61/740,520, filed on Dec. 21, 2012.

(51) Int. Cl.
| | | |
|---|---|---|
| *A61K 31/496* | (2006.01) | |
| *A61K 47/24* | (2006.01) | |
| *A61K 9/46* | (2006.01) | |
| *A61K 9/20* | (2006.01) | |
| *A61K 9/16* | (2006.01) | |

(52) U.S. Cl.
CPC .......... *A61K 31/496* (2013.01); *A61K 9/0007* (2013.01); *A61K 9/1611* (2013.01); *A61K 9/2009* (2013.01); *A61K 9/2054* (2013.01); *A61K 9/2077* (2013.01); *A61K 47/24* (2013.01)

(58) Field of Classification Search
CPC .. A61K 31/496; A61K 9/2054; A61K 9/2009; A61K 9/1611; A61K 47/24; A61K 9/0007; A61K 9/2077
See application file for complete search history.

(56) References Cited

U.S. PATENT DOCUMENTS

| | | | |
|---|---|---|---|
| 4,407,941 A | 10/1983 | Suginaka et al. | |
| 5,292,520 A | 3/1994 | de Haan et al. | |
| 5,498,630 A | 3/1996 | Phillion et al. | |
| 5,514,529 A | 5/1996 | Mihayashi et al. | |

(Continued)

FOREIGN PATENT DOCUMENTS

| | | |
|---|---|---|
| BE | 667399 | 11/1965 |
| EP | 1352650 A1 | 10/2003 |

(Continued)

OTHER PUBLICATIONS

Carter Pharmaceutials (https://web.archive.org/web/20101205132531/http://www.carterpharmaceuticalconsulting.com/articles/role-of-lubricants-in-solid-oral-dosage-manufacturing.html, accessed Aug. 1, 2017, published Dec. 5, 2010).*

(Continued)

*Primary Examiner* — Angela C Brown-Pettigrew

(57) ABSTRACT

There are provided pharmaceutical compositions comprising a compound of Formula (I) as defined herein and an amount of an alkaline effervescent agent that is sufficient to provide satisfactory in vitro dissolution; and further comprising one or more pharmaceutically acceptable ingredients; and to processes for obtaining them.

4 Claims, 5 Drawing Sheets

(56) References Cited

U.S. PATENT DOCUMENTS

| | | |
|---|---|---|
| 5,693,667 A | 12/1997 | Phillion et al. |
| 5,705,513 A | 1/1998 | Phillion et al. |
| 5,811,411 A | 9/1998 | Phillion et al. |
| 5,834,447 A | 11/1998 | Phillion et al. |
| 5,849,723 A | 12/1998 | Phillion et al. |
| 5,998,466 A | 12/1999 | Phillion et al. |
| RE36,562 E | 2/2000 | Phillion et al. |
| 6,028,101 A | 2/2000 | Phillion et al. |
| 6,133,252 A | 10/2000 | Phillion et al. |
| 6,165,507 A | 12/2000 | Phillion et al. |
| 6,248,894 B1 | 6/2001 | Phillion et al. |
| 6,252,078 B1 | 6/2001 | Phillion et al. |
| 6,271,237 B1 | 8/2001 | Galemmo, Jr. et al. |
| 6,407,114 B1 | 6/2002 | Bunnage et al. |
| 6,410,558 B1 | 6/2002 | Phillion et al. |
| 6,521,603 B2 | 2/2003 | Phillion et al. |
| 6,548,525 B2 | 4/2003 | Galemmo, Jr. et al. |
| 6,552,008 B1 | 4/2003 | Duffy et al. |
| 7,015,218 B1 | 3/2006 | Ushio et al. |
| 7,034,049 B1 | 4/2006 | Pevarello et al. |
| 7,115,359 B2 | 10/2006 | Usagawa et al. |
| 7,737,149 B2 | 6/2010 | Buttar et al. |
| 8,129,391 B2 | 3/2012 | Foote et al. |
| 2001/0046975 A1 | 11/2001 | Phillion et al. |
| 2002/0016326 A1 | 2/2002 | Galemmo, Jr. et al. |
| 2003/0225106 A1 | 12/2003 | Askew et al. |
| 2004/0043904 A1 | 3/2004 | Yamaguchi et al. |
| 2004/0087616 A1 | 5/2004 | Piotrowski et al. |
| 2004/0220170 A1 | 11/2004 | Atkinson et al. |
| 2004/0259877 A1 | 12/2004 | Muto et al. |
| 2005/0020564 A1 | 1/2005 | Atkinson et al. |
| 2005/0037298 A1 | 2/2005 | Usagawa et al. |
| 2005/0070589 A1 | 3/2005 | Ngu et al. |
| 2005/0176965 A1 | 8/2005 | Chen et al. |
| 2005/0209297 A1 | 9/2005 | Sanner et al. |
| 2005/0245518 A1 | 11/2005 | Delorme et al. |
| 2005/0256086 A1 | 11/2005 | Eyjolfsson |
| 2006/0004010 A1 | 1/2006 | Habashita et al. |
| 2006/0019958 A1 | 1/2006 | Muto et al. |
| 2006/0111409 A1 | 5/2006 | Muto et al. |
| 2006/0116395 A1 | 6/2006 | Piotrowski et al. |
| 2006/0122243 A1 | 6/2006 | Muto et al. |
| 2008/0038342 A1 | 2/2008 | Bergman et al. |
| 2008/0153812 A1 | 6/2008 | Butter et al. |
| 2009/0060996 A1 | 3/2009 | Kristjansson |
| 2012/0114753 A1* | 5/2012 | Yoo .................. A61K 9/0065 424/466 |
| 2014/0179712 A1 | 6/2014 | Baker et al. |

FOREIGN PATENT DOCUMENTS

| | | |
|---|---|---|
| EP | 1510207 A1 | 3/2005 |
| EP | 1510210 A1 | 3/2005 |
| EP | 1514544 A1 | 3/2005 |
| EP | 1541563 A1 | 6/2005 |
| GB | 843940 | 8/1960 |
| JP | 3310226 B4 | 11/1933 |
| JP | 63133152 A1 | 6/1988 |
| JP | 04184437 A | 7/1992 |
| JP | 07188269 A | 7/1995 |
| JP | 2890065 B2 | 2/1999 |
| JP | 0467645 A | 3/2004 |
| JP | 04292322 A | 10/2004 |
| WO | 1993019054 A1 | 9/1993 |
| WO | 1994015920 A1 | 7/1994 |
| WO | 1996014843 A2 | 5/1996 |
| WO | 1998028269 A1 | 7/1998 |
| WO | 1998052941 A1 | 11/1998 |
| WO | 1998052944 A1 | 11/1998 |
| WO | 2000049001 A2 | 8/2000 |
| WO | 2001012189 A1 | 2/2001 |
| WO | 2001012621 A1 | 2/2001 |
| WO | 2004098528 A2 | 11/2001 |
| WO | 2002066470 A1 | 8/2002 |
| WO | 2002088090 A2 | 11/2002 |
| WO | 2004007458 A1 | 1/2004 |
| WO | 2004071440 A2 | 8/2004 |
| WO | 2004098518 A2 | 11/2004 |
| WO | 2004099156 A1 | 11/2004 |
| WO | 2005021537 A1 | 3/2005 |
| WO | 2005048948 A2 | 6/2005 |
| WO | 2005051919 A1 | 6/2005 |
| WO | 2005105780 A1 | 11/2005 |
| WO | 2006116713 A1 | 11/2006 |
| WO | 2007016228 A2 | 2/2007 |
| WO | 2007038979 A1 | 4/2007 |
| WO | 2008075068 A2 | 6/2008 |
| WO | 2010030201 A2 | 3/2010 |
| WO | 2010121323 A1 | 10/2010 |
| WO | 2011019956 A2 | 2/2011 |
| WO | 2012052757 A1 | 4/2012 |

OTHER PUBLICATIONS

Wayback Machine (accessed Aug. 1, 2017).*
Arunachalam et al., Journal of Global Trends in Pharmaceutical Sciences, vol. 1, Issue 1, pp. 92-110, Oct.-Dec. 2010.
Bogolyubsky et al., Synthesis of 3-amino-5-oxy-1-(2,4,6-trichlorophenyl)-4-fluoropyrazole and its Acyl Derivatives, Ukr. Khim. Zhurn (Russian Edition) (1989), vol. 55, No. 4, pp. 420-423 (Eng translation).
Cavasotto et al., In Silico Identification of Novel EGFR Inhibitors with Antiproliferative Activity Against Cancer Cells, Bioorganic & Medicinal Chemistry Letters, 2006, vol. 16, pp. 1969-1974.
Fu and Shuttleworth, "Synthesis and Purification of 3-N-acylaminopyrazolines using a sequence of functionalized polymers," Tetrahedron Letters, 2003, vol. 44, pp. 3843-3845.
Hammad et al., "Synthesis of some new pyrazolones and benzimidazol-acetronitriles derived from Xanthene," Egyptian Journal of Chemistry, 1986, vol. 29, No. 6, pp. 617-622.
Javaid et al., J. Pharm Sci., vol. 61, No. 9., 1972, pp. 1370-1373.
Kataeva et al., Russian Journal of General Chemistry, 2003, vol. 73, No. 5, pp. 776-781.
Khattab, J. Pharm. Pharmacol., 1992, vol. 45, pp. 687-691.
Mukherjee, Food Chem. Toxicol., 1997, vol. 35, pp. 1177-1179.
Pevarello et al., '3-Aminopyrazole inhibitors of CDK2/Cyclin A as Antitumor Agents 1. Lead Finding, "J. Med. Chem., 2004, vol. 47, pp. 3367-3380 dihydropyrazol-5-one" Russian Journal of General Chemistry, 2003, vol. 73, No. 5, pp. 776-781.
Rolls, Am. J. Clin. Nutr., 1991, vol. 53, pp. 872-878.
Velmurugan et al., International Journal of Chemical and Pharmaceutical Sciences, Dec. 2010, vol. 1(2).
Weissberger et al., Journal of the American Chemical Society, 1944, vol. 66, pp. 1851-1855.
Zhang et al., Clin Cancer Research, vol. 18, No. 24, Oct. 18, 2012, pp. 6658-6667.

* cited by examiner

PHARMACEUTICAL FORMULATION OF N-[5-[2-(3,5-DIMETHOXYPHENYL) ETHYL]-2H-PYRAZOL-3-YL]-4-[(3R,5S)-3,5-DIMETHYLPIPERAZIN-1-YL] BENZAMIDE

This application is a continuation of U.S. application Ser. No. 14/108,595, filed on Dec. 17, 2013, which claims the benefit under 35 U.S.C. § 119(e) of Application No. U.S. 61/740,520 filed on 21 Dec. 2012.

FIELD OF THE INVENTION

The present invention relates to pharmaceutical/formulation chemistry. The invention is understood to apply generally to formulations of compounds which contain an increased percent loading of the active ingredient. As a preferred aspect, provided herein are formulations of N-[5-[2-(3,5-dimethoxyphenyl)ethyl]-2H-pyrazol-3-yl]-4-[(3R,5S)-3,5-dimethylpiperazin-1-yl]benzamide (Compound I) which exhibit satisfactory manufacturability, stability and in vitro dissolution. The formulations are useful for treating of cancer.

BACKGROUND OF THE INVENTION

In the manufacture of pharmaceutical formulations for oral administration, it may be desirable for the drug to dissolve rapidly soon after administration. However, it is known that certain physic-chemical properties of the drug, such as particle size, wettability, or solubility, may lead to a pharmaceutical formulation which exhibits unsatisfactory and/or variable dissolution or to a formulation which exhibits unsatisfactory and/or variable bioavailability. Such formulations may be unsuitable for use by patients.

Compound I (below) is disclosed in international patent application

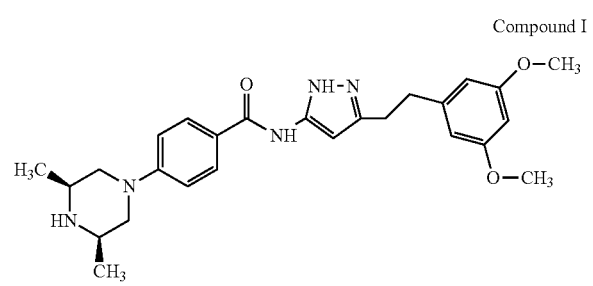

Compound I for use in the treatment of cancer.

Javaid et al (J. Pharm. Sci. 61 (9) 1972 pp 1370-1373) studied the effect of various classes of buffering agents on the dissolution of aspirin from tablet formulations. Compound I is currently in clinical studies for the treatment of cancer, in particular cancers of the lung, breast, gatric and bladder. Dosing is currently done with orally delivered tablets with tablet strengths of 20 and 100 mg. These tablets exhibit satisfactory dissolution across the physiological pH range. However, the manufacturing process used for clinical batches cannot be operated at commercial scale, due to a high incidence of filming which cannot be corrected using conventional means. It is desirable, therefore, to produce new pharmaceutical formulations of Compound I which overcome at least in part the above problems.

DESCRIPTION OF THE INVENTION

This invention is generally directed to formulations of compounds with improved manufacturability, in particular to formulations which contain an alkaline effervescent excipient and which exhibit satisfactory dissolution across the physiological pH range.

The compound of formula (I) (known hereafter as "Formula (I)") is shown below:

Formula (I)

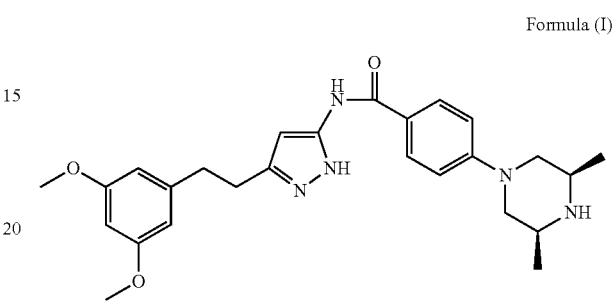

The compound of Formula (I) is a base and exhibits pH dependent solubility, having a solubility in simulated gastric fluid (pH 1.2) of approximately 5 mg/mL ('slightly soluble', using the definition given in the United States Pharmacopeia/National Formulary, USP35-NF30), which reduces in fasted simulated intestinal fluid (pH 6.5) to approximately 0.25 mg/mL ('very slightly soluble' by the USP definition). Furthermore, we have observed that the compound of Formula (I) may form a viscous material at low pH, which has the effect of reducing the rate at which the drag dissolves. In order to achieve an acceptable rate and extent of dissolution across the physiological pH range, the earlier clinical formulation was manufactured using conditions designed to give a fine granule which, when compressed into tablet form would disperse rapidly upon administration. While this approach did result in an improvement in dissolution performance, 'filming' problems were experienced during manufacture. In addition, it was observed that the use of conventional lubricants such as magnesium stearate and sodium stearyl fumarate led to chemical degradation including impurity formation and/or complexation.

It was unexpectedly found that alkaline effervescent excipients were effective in both improving the rate and extent of dissolution at low pH, despite the reduction in solubility under alkaline conditions, and in ameliorating the "filming" issues. A further unexpected finding was that the use of an alternative lubricant, glyceryl dibehenale, was effective in ameliorating chemical degradation.

In particular, this invention is directed at least in part to the unexpected result that the use of an alkaline effervescent excipient with Formula (I) in the formulation allows the manufacture of tablets with improved manufacturability and/or a satisfactory dissolution across the physiological pH range; and, at least in part, to the unexpected result that an alternative lubricant allows the manufacture of tablets with improved stability.

In a further aspect, this invention provides the use of an alkaline effervescent excipient with Formula (I) in the formulation allowing the manufacture of tablets with improved manufacturability and/or a satisfactory dissolution across the physiological pH range.

In a still further aspect, this invention provides the use of magnesium carbonate with Formula (I) in the formulation allowing the manufacture of tablets with improved manufacturability and/or a satisfactory dissolution across the physiological pH range. In a still further aspect, this invention provides the use of calcium carbonate with Formula (I) in the formulation allowing the manufacture of tablets with improved manufacturability and/or a satisfactory dissolution across the physiological pH range.

In a still further aspect, this invention provides the use of sodium bicarbonate with Formula (I) in the formulation allowing the manufacture of tablets with improved manufacturability and/or a satisfactory dissolution across the physiological pH range.

In a further aspect, this invention provides the use of an alternative lubricant with Formula (I) in the formulation allowing the manufacture of tablets with improved stability.

In a still further aspect, this invention provides the use of glyceryl dibehenate with Formula (I) in the formulation allowing the manufacture of tablets with improved stability.

In a further aspect of the invention, there is provided a pharmaceutical composition comprising greater than 10% w/w of Formula (I) and an amount of an alkaline effervescent excipient that is sufficient to provide satisfactory in vitro dissolution; and further comprising one or more pharmaceutically acceptable ingredients.

In another aspect of the invention, there is provided a pharmaceutical composition in unit dosage form comprising from 10 mg to 200 mg of Formula (I) (for example 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg or 200 mg) and an amount of an alkaline effervescent excipient that is sufficient to provide satisfactory in vitro dissolution; and further comprising one or more pharmaceutically acceptable ingredients. For the avoidance of doubt, each of the previous integers represents a separate and independent aspect of the invention.

In another aspect of the invention a unit dosage form of the pharmaceutical composition comprises between about 10 mg to about 160 mg of Formula (I).

In another aspect of the invention a unit dosage form of the pharmaceutical composition comprises between about 10 mg to about 140 mg of Formula (I).

In a still further aspect, a unit dosage form of the pharmaceutical composition comprises between about 10 mg to about 130 mg of Formula (I).

In a yet further aspect, a unit dosage form of the pharmaceutical composition comprises between about 15 mg to about 110 mg of Formula (I).

In a specific aspect of the invention, a unit dosage form of the pharmaceutical composition comprises 20 mg±1 mg of Formula (I).

In a further specific aspect of the invention, a unit dosage form of the pharmaceutical composition comprises 80 mg±4 mg of Formula (I).

In a further specific aspect of the invention, a unit dosage form of the pharmaceutical composition comprises 100 mg±5 mg of Formula (I).

In a further specific aspect of the invention, a unit dosage form of the pharmaceutical composition comprises 160 mg±8 mg of Formula (I).

In a further specific aspect of the invention, a unit dosage form of the pharmaceutical composition comprises 200 mg±10 mg of Formula (I).

In another aspect of the invention the pharmaceutical composition comprises between 10% w/w to 60% w/w of Formula (I).

In a further aspect, the pharmaceutical composition comprises between 15% w/w to 50% w/w of Formula (I).

In a still further aspect, the pharmaceutical composition comprises between 15% w/w to 45% w/w of Formula (I).

In a still further aspect, the pharmaceutical composition comprises between 15% w/w to 40% w/w of Formula (I).

In a still further aspect, the pharmaceutical composition comprises between 15% w/w to 25% w/w of Formula (I).

In another aspect of the invention the pharmaceutical composition comprises about 20% w/w of Formula (I).

In a specific aspect of the invention, the pharmaceutical composition comprises 21.33%±5% w/w of Formula (I).

In a further aspect, the pharmaceutical composition comprises between 20.26% w/w to 22.40% w/w of Formula (I).

In a still further aspect of the invention, the pharmaceutical composition comprises from 1% w/w to 50% w/w of an alkaline effervescent excipient In a still further aspect of the invention, the pharmaceutical composition comprises from 1% w/w to 40% w/w of an alkaline effervescent excipient In a further aspect, the pharmaceutical composition comprises from 10% w/w to, 30% w/w of an alkaline effervescent excipients.

In a still further aspect, the pharmaceutical composition comprises about 20% w/w of an alkaline effervescent excipients.

In a further aspect, the pharmaceutical composition comprises from 15% w/w to 20% w/w of an alkaline effervescent excipients.

In a still further aspect of the invention, the pharmaceutical composition comprises less than or equal to 6% w/w of a conventional lubricant Alternatively the use of an alternative lubricant may improve stability.

In a still further aspect of the invention, the pharmaceutical composition comprises less than or equal to 5% w/w of an alternative lubricant In a still further aspect of the invention, the pharmaceutical composition comprises less than or equal to 4% w/w of an alternative lubricant In a further aspect, the pharmaceutical composition comprises less than or equal to 3% w/w of an alternative lubricant.

In a still further aspect of the invention, the pharmaceutical composition comprises between 0.25% w/w and 8% w/w of an alternative lubricant.

In a still further aspect of the invention, the pharmaceutical composition comprises between 0.5% w/w and 5% w/w of an alternative lubricant.

In a still further aspect of the invention, the pharmaceutical composition comprises between 1% w/w and 4% w/w of an alternative lubricant.

In a still further aspect of the invention, the pharmaceutical composition comprises between 2.5% w/w and 3.5% w/w of an alternative lubricant.

In a further aspect, the pharmaceutical composition comprises about 3% w/w of an alternative lubricant.

In a further aspect of the invention, there is provided a pharmaceutical composition comprising greater than 10% w/w of Formula (I) and less than or equal to 50% w/w of an alkaline effervescent excipient; and further comprising one or more pharmaceutically acceptable ingredients.

In a further aspect of the invention, there is provided a pharmaceutical composition comprising greater than 15% w/w of Formula (I) and less than or equal to 40% w/w of an alkaline effervescent excipient; and further comprising one or more pharmaceutically acceptable ingredients.

In a further aspect of the invention, there is provided a pharmaceutical composition comprising greater than 15% w/w of Formula (I) and less than or equal to 30% w/w of an alkaline effervescent excipient; and further comprising one or more pharmaceutically acceptable ingredients.

In a further aspect of the invention, there is provided a pharmaceutical composition comprising greater than 15% w/w of Formula (I) and less than or equal to 20% w/w of an alkaline effervescent excipient; and further comprising one or more pharmaceutically acceptable ingredients.

In a further aspect of the invention, there is provided a pharmaceutical composition comprising from 10% w/w to 50% w/w of Formula (I) and from 1% w/w to 50% w/w of an alkaline effervescent excipient; and optionally further comprising one or more pharmaceutically acceptable ingredients.

In a further aspect of the invention, there is provided a pharmaceutical composition comprising from 15% w/w to 35% w/w of Formula (I) and from 10% to 40% w/w of an alkaline effervescent excipient; and further comprising one or more pharmaceutically acceptable ingredients.

In a further aspect of the invention, there is provided a pharmaceutical composition comprising from 15% w/w to 25% w/w of Formula (I) and from 15% w/w to 25% w/w of an alkaline effervescent excipient; and further comprising one or more pharmaceutically acceptable ingredients.

In a further aspect of the invention, there is provided a pharmaceutical composition comprising about 20% w/w of Formula (I) and about 20% w/w of an alkaline effervescent excipient; and further comprising one or more pharmaceutically acceptable ingredients.

In a further aspect of the invention, there is provided a unit dosage form comprising from 15% w/w to 45% w/w of Formula (I) and from 10% to 40% w/w of an alkaline effervescent excipients and further comprising one or more pharmaceutically acceptable ingredients, wherein the unit comprises from 10 to 200 mg of Formula (I)

In a further aspect of the invention, there is provided a unit dosage form comprising from 15% w/w to 40% w/w of Formula (I) and from 10% to 40% w/w of an alkaline effervescent excipients and further comprising one or more pharmaceutically acceptable ingredients, wherein the unit comprises from 10 to 200 mg of Formula (I).

In a further aspect of the invention, there is provided a unit dosage form comprising from 15% w/w to 25% w/w of Formula (I) and from 15% to 25% w/w of an alkaline effervescent excipients and further comprising one or more pharmaceutically acceptable ingredients, wherein the unit comprises 20 mg of Formula (I).

In a further aspect of the invention, there is provided a unit dosage form comprising from 15% w/w to 25% w/w of Formula (I) and from 15% to 25% w/w of an alkaline effervescent excipients and further comprising one or more pharmaceutically acceptable ingredients, wherein the unit comprises 80 mg of Formula (I).

In a further aspect of the invention, there is provided a unit dosage form comprising from 15% w/w to 25% w/w of Formula (I) and from 15% to 25% w/w of an alkaline effervescent excipients and further comprising one or more pharmaceutically acceptable ingredients, wherein the unit comprises 160 mg of Formula (I).

In a further aspect of the invention, optional ingredients which can be added to the pharmaceutical composition include one or more of the following:
a) fillers;
b) binding agents;
c) lubricants; and
d) disintegrants.

Where optional ingredients are added to make up the remainder of the pharmaceutical composition, the remainder may optionally include one or more of the following:
a) fillers which, when employed, range between for example about 10 to about 75 weight percent (e.g. about 15 to about 70 weight percent) of the remainder of the dry formulation;
b) binding agents which, when employed range between for example about 2 to about 8 weight percent of the remainder of the dry formulation;
c) lubricants which, when employed, range from between about 0.25 and 5 weight percent of the remainder of the dry formulation; and
d) disintegrants which, when employed, range from between about 0.5 and 10.0 weight percent (e.g. about 5 weight percent) of the remainder of the dry formulation.

In a further aspect of the invention, the pharmaceutical composition further comprises one or more additional ingredients independently selected from, for example
a) fillers such as mannitol (e.g. Pearlitol 50c, Peralitol 120c or Pearlitol 160c) or microcrystalline celluloses (e.g. MCC Avicel PH 101, Emcocel 90M, etc.);
b) binding agents such as Plasdone K29/32, Povidone, microcrystalline celluloses or Kollidon K30;
c) lubricants such as glyceryl dibehenate; and
d) disintegrants such as sodium starch glycolate, for example ExploTab or Glycolys LV.

In a further aspect of the invention, there is provided a pharmaceutical composition comprising from 15% w/w to 25% w/w of Formula (I), from 15% w/w to 25% w/w of an alkaline effervescent excipients, from 2.5% w/w to 3.5% w/w of an alternative lubricant; and further comprising from 40% w/w to 60% filler w/w, from 1% w/w to 3% w/w binder and 5% w/w to 9% w/w disintegrant.

In another aspect of the invention, there is provided a tablet comprising greater than 10% w/w of Formula (I) and an amount of an alkaline effervescent excipient that is sufficient to provide satisfactory in vitro dissolution; and further comprising one or more pharmaceutically acceptable ingredients.

In another aspect of the invention, there is provided a tablet comprising from 10 mg to 200 mg of Formula (I) (for example 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg 190 mg or 200 mg) and an amount of an alkaline effervescent excipient that is sufficient to a provide satisfactory in vitro dissolution; and further comprising one or more pharmaceutically acceptable ingredients. For the avoidance of doubt, each of the previous integers represents a separate and independent aspect of the invention.

In another aspect of the invention, the tablet comprises between about 10 mg to about 160 mg of Formula (I).

In another aspect of the invention the tablet comprises between about 10 mg to about 140 mg of Formula (I).

In a still further aspect, the tablet comprises between about 10 mg to about 130 mg of Formula (I).

In a still further aspect, the tablet comprises between about 15 mg to about 110 mg of Formula (I).

In a specific aspect of the invention, the tablet comprises 20 mg±1 mg of Formula (I).

In a further specific aspect of the invention, the tablet comprises 80 mg±4 mg of Formula (I).

In a further specific aspect of the invention, the tablet comprises 100 mg±5 mg of Formula (I).

In a further specific aspect of the invention, the tablet comprises 160 mg±8 mg of Formula (I).

In a further specific aspect of the invention, the tablet comprises 200 mg±10 mg of Formula (I).

In a still further aspect of the invention, the tablet comprises from 1% w/w to 50% w/w of an alkaline effervescent excipient In a still further aspect of the invention, the tablet comprises from 1% w/w to 40% w/w of an alkaline effervescent excipient In a further aspect, the tablet comprises from 10% w/w to 30% w/w of an alkaline effervescent excipients.

In a still further aspect, the tablet comprises about 20% w/w of an alkaline effervescent excipients.

In a specific aspect of the invention, the tablet comprises 21.33%±5% w/w of Formula (I).

In a further aspect, the tablet comprises between 20.26% w/w to 22.40% w/w of Formula (I).

In a still further aspect, the tablet comprises between about 15% w/w to about 25% w/w of Formula (I).

In a still farther aspect of the invention, the tablet comprises less than or equal to 50% w/w of an alkaline effervescent excipient.

In a further aspect, the tablet comprises less than or equal to 40% w/w of an alkaline effervescent excipient.

In a further aspect, the tablet comprises less than or equal to 30% w/w of an alkaline effervescent excipient.

In a still further aspect, the tablet comprises less than or equal to 20% w/w of an alkaline effervescent excipient.

In a further aspect of the invention, the tablet comprises less than or equal to 6% w/w of a conventional lubricant.

Alternatively the use of an alternative lubricant may improve stability.

In a still further aspect of the invention, the tablet comprises less than or equal to 5% w/w of an alternative lubricant.

In a still further aspect of the invention, the tablet comprises less than or equal to 4% w/w of an alternative lubricant.

In a further aspect, the tablet comprises less than or equal to 3% w/w of an alternative lubricant.

In a still further aspect of the invention, the tablet comprises between 0.25% w/w and 8% w/w of an alternative lubricant.

In a still further aspect of the invention, the tablet comprises between 0.5% w/w and 5% w/w of an alternative lubricant.

In a still further aspect of the invention, the tablet comprises between 1% w/w and 4% w/w of an alternative lubricant.

In a still further aspect of the invention, the tablet comprises between 2.5% w/w and 3.5% w/w of an alternative lubricant.

In a further aspect, the tablet comprises about 3% w/w of an alternative lubricant.

In a further aspect of the invention, there is provided a tablet comprising from 10% w/w to 50% w/w of Formula (I) and from 1% w/w to 50% w/w of an alkaline effervescent excipient; and optionally further comprising one or more pharmaceutically acceptable ingredients.

In a further aspect of the invention, there is provided a tablet comprising from 15% w/w to 35% w/w of Formula (I) and from 10% to 40% w/w of an alkaline effervescent excipient; and further comprising one or more pharmaceutically acceptable ingredients.

In a further aspect of the invention, there is provided a tablet comprising from 15% w/w to 25% w/w of Formula (I) and from 15% w/w to 25% w/w of an alkaline effervescent excipient; and further comprising one or more pharmaceutically acceptable ingredients.

In a further aspect of the invention, there is provided a tablet comprising about 20% w/w of Formula (I) and about 20% w/w of an alkaline effervescent excipient; and further comprising one or more pharmaceutically acceptable ingredients.

In a further aspect of the invention, there is provided a tablet comprising from 15% w/w to 45% w/w of Formula (I) and from 10% to 40% w/w of an alkaline effervescent excipients and further comprising one or more pharmaceutically acceptable ingredients, wherein the tablet comprises from 10 to 200 mg of Formula (I)

In a further aspect of the invention, there is provided a tablet comprising from 15% w/w to 40% w/w of Formula (I) and from 10% to 40% w/w of an alkaline effervescent excipients and further comprising one or more pharmaceutically acceptable ingredients, wherein the tablet comprises from 10 to 200 mg of Formula (I).

In a further aspect of the invention, there is provided a tablet comprising from 15% w/w to 25% w/w of Formula (I) and from 15% to 25% w/w of an alkaline effervescent excipients and further comprising one or more pharmaceutically acceptable ingredients, wherein the tablet comprises 20 mg of Formula (I).

In a further aspect of the invention, there is provided a tablet comprising from 15% w/w to 25% w/w of Formula (I) and from 15% to 25% w/w of an alkaline effervescent excipients and further comprising one or more pharmaceutically acceptable ingredients, wherein the tablet comprises 80 mg of Formula (I).

In a further aspect of the invention, there is provided a tablet comprising from 15% w/w to 25% w/w of Formula (I) and from 15% to 25% w/w of an alkaline effervescent excipients and further comprising one or more pharmaceutically acceptable ingredients, wherein the tablet comprises 160 mg of Formula (I).

The dosage forms of this invention may include one or more pharmaceutically acceptable excipients which may be selected, for example, from adjuvants, carriers, binders, lubricants, diluents, stabilising agents, buffering agents, emulsifying agents, viscosity-regulating agents, surfactants, preservatives, flavourings or colorants. It will be understood that an individual excipient may be multifunctional. Examples of pharmaceutically acceptable excipients are described in the Handbook of Pharmaceutical Excipients (Fifth Edition, 2005, edited by Ray C. Rowe, Paul J. Sheskey and Sian C. Owen, published by the American Pharmaceutical Association and the Pharmaceutical Press). As will be understood by those skilled in the art, the most appropriate method of administering the active ingredients is dependent on a number of factors.

It will be understood that the therapeutic dose of each active ingredient administered in accordance with the present invention will vary depending upon the particular active ingredient employed, the mode by which the active ingredient is to be administered, and the condition or disorder to be treated.

In a further aspect of the invention, optional ingredients which can be added to make up the remainder of the tablet include one or more of the following:

a) fillers which, when employed, range between for example about 10 to about 75 weight percent (e.g. about 15 to about 70 weight percent) of the remainder of the tablet formulation;

b) binding agents which, when employed range between for example about 2 to about 8 weight percent of the remainder of the tablet formulation;
c) lubricants which, when employed, range from between about 0.25 and 3.5 weight percent of the remainder of the tablet formulation; and
d) disintegrants which, when employed, range from between about 0.5 and 10.0 weight percent (e.g. about 5 weight percent) of the remainder of the tablet formulation.

In a further aspect of the invention, the tablet further comprises one or more additional ingredients independently selected from, for example:
a) fillers such as mannitol (e.g. Pearlitol 50c, Peralitol 120c or Pearlitol 160c) or microcrystalline celluloses (e.g. MCC Avicel PH 101, Emcocel 90M, etc.);
b) binding agents such as Plasdone K29/32, Povidone, microcrystalline celluloses or Kollidon K30;
c) lubricants such as glyceryl dibehenate;
d) disintegrants such as sodium starch glycolate, for example ExploTab or Glycolys LV;

In a further aspect of the invention, the tablet optionally further comprises a suitable coating, for example a film coating. A coating can be used to provide protection against, for example, moisture ingress or degradation by light, to colour the formulation, or to modify or control the release of Formula (I) from the formulation.

In a yet further aspect of the invention, the pharmaceutical composition comprises the following components by weight:

| Composition A (mg) | | Composition B (mg) | |
| --- | --- | --- | --- |
| Formula (I) | 20.00 | Formula (I) | 80.00 |
| Microcrystalline cellulose | 14.06 | Microcrystalline cellulose | 56.25 |
| Mannitol | 29.22 | Mannitol | 116.87 |
| Magnesium carbonate | 18.75 | Magnesium carbonate | 75.00 |
| Hydroxypropyl cellulose | 1.88 | Hydroxypropyl cellulose | 7.50 |
| Sodium starch glycollate | 7.03 | Sodium starch glycollate | 28.13 |
| Glyceryl dibehenate | 2.81 | Glyceryl dibehenate | 11.25 |

In a yet further aspect of the invention, the pharmaceutical composition comprises the following components (% w/w):

| Compositions A and B (% w/w) | |
| --- | --- |
| Formula (I) | 21.33 |
| Microcrystalline cellulose | 15.00 |
| Mannitol | 31.17 |
| Magnesium carbonate | 20.00 |
| Hydroxypropyl cellulose | 2.00 |
| Sodium starch glycollate | 7.50 |
| Glyceryl dibehenate | 3.00 |

In a still further aspect, the invention comprises a tablet formed from the pressing of composition A and/or composition B into tablet form.

In a further aspect of the invention, there is provided a process for the preparation of a pharmaceutical composition which process comprises the following steps:
Step A—comprises mixing Formula (I) with an alkaline effervescent excipient optionally in the presence of one or more pharmaceutically acceptable ingredients. In a further aspect, Step A is carried out in the presence of one or more additional fillers (such as mannitol) and optionally in the presence of one or more pharmaceutically acceptable ingredients. In a still further aspect, Step A is carried out in the presence of one or more additional fillers (such as mannitol) and optionally in the presence of one or more binding agents and/or one or more disintegrants.
Step B—comprises adding purified water and/or binder solution into the powder mixture from Step A above and mixing to form granules and optionally passing through a filter screen to break-up agglomerates. In a further aspect between about 10% and 45% by weight of purified water is added into the powder mixture.
Step C—comprises drying the granules produced in Step B above until an LOD of less than 10% (e.g. less than 5%) is achieved, to provide dried granules.
Step D—comprises optionally milling the dried granules from Step C.
Step E—optionally, comprises mixing the milled granules from Step D with an alkaline effervescent excipient.

In a farther aspect of the invention there is provided a process for the preparation of a pharmaceutical composition which process (wet granulation process) comprises:
a) blending Formula (I) with an effervescent agent, one or more additional fillers (such as mannitol) and optionally in the presence of one or more binding agents and/or one or more disintegrants and/or one or more other excipients;
b) adding between about 10% and 45% by weight of purified water and/or binder solution into the powder mixture of a) above and mixing to form enlarged granules and optionally passing through a filter screen to break-up large agglomerates; and
c) drying the enlarged granules produced in b) above until an LOD of less than 10% (e.g. less than 5%) is achieved, to provide dried granules.

Alternatively, in another aspect of the invention, there is provided a process for the preparation of a pharmaceutical composition which process comprises the following steps
Step A—mixing Formula (I) optionally with an alkaline effervescent excipient optionally in the presence of one or more pharmaceutically acceptable ingredients. In a further aspect, Step A is carried out in the presence of one or more additional fillers (such as mannitol) and optionally in the presence of one or more pharmaceutically acceptable ingredients. In a still further aspect, Step A is carried out in the presence of one or more additional fillers (such as mannitol) and optionally in the presence of one or more binding agents and/or one or more disintegrants.
Step B—comprises adding purified water and/or binder solution into the powder mixture from Step A above and mixing to form granules and optionally passing through a filter screen to break-up agglomerates. Typically, between about 10% and 45% by weight of purified water and/or binder solution is added into the powder mixture.
Step C—comprises drying the granules produced in Step B above until an LOD of less than 10% (e.g. less than 5%) is achieved, to provide dried granules.
Step D—comprises milling the dried granules from Step C to give milled granules
Step E—comprises mixing the milled granules from Step D with an effective amount of an alkaline effervescent excipient.

In a further aspect of the invention there is provided a process for the preparation of a pharmaceutical composition which process (wet granulation process) comprises:
a) blending Formula (I) with one or more additional fillers (such as mannitol) and optionally in the presence of one or more binding agents and/or one or more disintegrants and/or one or more other excipients;

b) adding between about 10% and 45% by weight of purified water and/or binder solution into the powder mixture of a) above and mixing to form granules and optionally passing through a filter screen to break-up agglomerates;

c) drying the granules produced in b) above until an LOD of less than 10% (e.g. less than 5%) is achieved, to provide dried granules;

d) milling the dried granules produce in c) to give milled granule; and e) mixing the milled granules from d) with an alkaline effervescent excipient.

In another of its method aspects, this invention further comprises milling the dried granules. In one aspect, the dried granules are milled so that about 90 weight percent have a particle size between about 25 µm to about 3500 µm in diameter.

In yet another aspect, the dried, milled, granules are mixed with a conventional and/or alternative lubricant, and then the resulting pharmaceutical composition is tabletted. Conventional and alternative lubricants include glyceryl dibehenate, sodium stearyl fumarate, magnesium stearate, colloidal silica and talc.

In a further aspect of the invention, the alternative lubricant (such as glyceryl dibehenate) can be added to the dry granules prior to milling, and then the resulting pharmaceutical composition is milled and then tabletted.

In another aspect, this invention provides a wet granulated formulation comprising between 10% w/w to 60% w/w of Formula (I) and an amount of an alkaline effervescent excipient that is sufficient to provide satisfactory in vitro dissolution; and further comprising one or more pharmaceutically acceptable ingredients.

In another aspect of the invention the wet granulated formulation comprises between 15% w/w to 50% w/w of Formula (I).

In a further aspect, the wet granulated formulation comprises between 15% w/w to 40% w/w of Formula (I).

In a further aspect, the wet granulated formulation comprises between 15% w/w to 25% w/w of Formula (I).

In another aspect of the invention the wet granulated formulation comprises about 20% w/w of Formula (I).

In a specific aspect of the invention, the wet granulated formulation contains 21.33%±5% w/w of Formula (I).

In a further aspect, the wet granulated formulation comprises between 20.26% w/w to 22.40% w/w of Formula (I).

In a still further aspect of the invention, the wet granulated formulation comprises from 1% w/w to 50% w/w of an alkaline effervescent excipient.

In a further aspect, the wet granulated formulation comprises from 1% w/w to 40% w/w of an alkaline effervescent excipient.

In a further aspect, the wet granulated formulation comprises from 10% w/w to 30% w/w of an alkaline effervescent excipient In a still further aspect, the wet granulated formulation comprises from 15% w/w to 25% w/w of an alkaline effervescent excipient In a still further aspect, the wet granulated formulation comprises about 20% w/w of an alkaline effervescent excipient In a further aspect of the invention, there is provided a wet granulation formulation comprising from 10% w/w to 50% w/w of Formula (I) and from 1% w/w to 50% w/w of an effervescent agent; and further comprising one or more pharmaceutically acceptable ingredients.

In a further aspect of the invention, there is provided a wet granulation formulation comprising greater from 10% w/w to 45% w/w of Formula (I) and from 10% w/w to 45% w/w of an alkaline effervescent excipient; and further comprising one or more pharmaceutically acceptable ingredients.

In a further aspect of the invention, there is provided a wet granulation formulation comprising from 15% w/w to 25% w/w of Formula (I) and from 15% to 25% w/w of an alkaline effervescent excipient; and further comprising one or more pharmaceutically acceptable ingredients.

In a further aspect of the invention, there is provided a wet granulation formulation comprising about 20% w/w of Formula (I) and about 20% w/w of an alkaline effervescent excipient; and further comprising one or more pharmaceutically acceptable ingredients.

In another aspect of the invention the wet granulation formulation comprises Formula (I), water, an alkaline effervescent excipient, additional filler(s), binding agent(s) and disintegrant(s).

In another aspect, this invention provides a tablet formed by compressing the wet granulated formulation.

In a further aspect of the invention, there is provided a further process for the preparation of a pharmaceutical composition as defined above which process comprises passing the mixture of Step A above through a compactor to produce dry granules (Step D).

In a further aspect of the present invention there is provided a process for the manufacture of a pharmaceutical composition which process (roller compaction process) comprises:

(a) blending Formula (I) with an alkaline effervescent excipient, one or more additional fillers (such as mannitol) and optionally in the presence of one or more binding agents and/or one or more disintegrants and/or one or more other excipients;

(b) passing the mixture of (a) above through a compactor to produce dry granules.

In another of its method aspects, this invention further comprises milling the dried granules. In one aspect, the dried granules are milled so that about 90 weight percent have a particle size between about 25 µm to about 3500 µm in diameter.

In yet another aspect, the dried, milled, granules are mixed with a lubricant, and then the resulting pharmaceutical composition is tabletted. Suitable lubricants include glyceryl dibehenate, sodium stearyl fumarate, magnesium stearate, colloidal silica and talc.

In yet another aspect of the present invention there is provided a process for the manufacture of a pharmaceutical composition which process (roller compaction process) comprises:

(a) blending Formula (I) with an alkaline effervescent excipient, one or more additional fillers (such as mannitol) and optionally in the presence of one or more binding agents and/or one or more disintegrants and/or one or more other excipients;

(b) passing the mixture of (a) above through a compactor to produce dry granules.

In another of its method aspects, this invention further comprises milling the dried granules. In one aspect, the dried granules are milled so that about 90 weight percent have a particle size between about 25 µm to about 3500 µm in diameter.

In yet another aspect of the present invention there is provided a process for the manufacture of a pharmaceutical composition which process (roller compaction process) comprises:

(a) blending Formula (I) optionally with an alkaline effervescent excipient, one or more additional fillers (such as mannitol) and optionally in the presence of one or more binding agents and/or one or more disintegrants and/or one or more other excipients;

(b) passing the mixture of (a) above through a compactor to produce dry granules.

The dried, milled, granules are then mixed with an alkaline effervescent excipient.

In yet another aspect, the dried, milled, granules are mixed with a lubricant, and then the resulting pharmaceutical composition is tabletted. Suitable lubricants include glyceryl dibehenate, sodium stearyl fumarate, magnesium stearate, colloidal silica and talc.

In an alternative aspect of the invention, the lubricant (such as glyceryl dibehenate) can be added to the dry granules prior to milling, and then the resulting pharmaceutical composition is milled and then tabletted.

In another aspect, this invention provides a roller compaction formulation comprising greater than 10% w/w of Formula (I) and an amount of an alkaline effervescent excipient that is sufficient to provide satisfactory in vitro dissolution; and further comprising one or more pharmaceutically acceptable ingredients.

In another aspect of the invention the roller compaction formulation comprises between 10% w/w to 60% w/w of Formula (I).

In a further aspect, the roller compaction formulation comprises between 15% w/w to 50% w/w of Formula (I).

In a still further aspect, the roller compaction formulation comprises between 15% w/w to 45% w/w of Formula (I).

In a still further aspect, the roller compaction formulation comprises between 15% w/w to 40% w/w of Formula (I).

In a still further aspect, the roller compaction formulation comprises between 15% w/w to 25% w/w of Formula (I).

In another aspect of the invention the roller compaction formulation comprises about 20% w/w of Formula (I).

In a specific aspect of the invention, the roller compaction formulation contains 21.33%±5% w/w of Formula (I).

In a further aspect, the roller compaction formulation contains 20.26% w/w to 22.40% w/w of Formula (I).

In a still further aspect of the invention, the roller compaction formulation comprises from 1% w/w to 50% w/w of an alkaline effervescent excipient.

In a further aspect, the roller compaction formulation comprises from 1% w/w to 40% w/w of an alkaline effervescent excipient.

In a still further aspect, the roller compaction formulation comprises from 10% w/w to 30% w/w of an alkaline effervescent excipient.

In a still further aspect, the roller compaction formulation comprises from 15% w/w to 25% w/w of an alkaline effervescent excipient.

In a still further aspect, the roller compaction formulation comprises about 20% w/w of an alkaline effervescent excipient.

In a further aspect of the invention, there is provided a roller compaction formulation comprising from 15% w/w to 45% of Formula (I) and from 10% w/w to 40% w/w of an alkaline effervescent excipient; and further comprising one or more pharmaceutically acceptable ingredients.

In a further aspect of the invention, there is provided a roller compaction formulation comprising from 15% w/w to 25% w/w of Formula (I) and from 15% w/w to 25% w/w of an alkaline effervescent excipient; and further comprising one or more pharmaceutically acceptable ingredients.

In another aspect of the invention the roller compaction formulation comprises Formula (I), an alkaline effervescent excipient, additional filler(s), binding agent(s) and disintegrant(s).

In another aspect, this invention provides a tablet formed by compressing the roller compaction formulation.

In a further aspect of the invention there is provided a process for the manufacture of a pharmaceutical composition which process (direct compression process) comprises:

(a) blending Formula (I) with an alkaline effervescent excipient, one or more additional fillers (such as mannitol) and optionally in the presence of one or more binding agents and/or one or more disintegrants and/or one or more lubricants and/or one or more other excipients;

(b) compressing the mixture of (a) above.

In another aspect of the invention the direct compression formulation comprises Formula (I), an alkaline effervescent excipient, additional filler(s), binding agent(s), lubricant(s) and disintegrant(s).

In another aspect, this invention provides a tablet formed directly by compressing the mixture of (a) above.

In another aspect, this invention provides a direct compression formulation comprising greater than 10% w/w of Formula (I) and an amount of an alkaline effervescent excipient that is sufficient to provide satisfactory in vitro dissolution; and further comprising one or more pharmaceutically acceptable ingredients.

In another aspect of the invention the direct compression formulation comprises between 10% w/w to 60% w/w of Formula (I).

In a further aspect, the direct compression formulation comprises between 10% w/w to 50% w/w of Formula (I).

In a still further aspect, the direct compression formulation comprises between 15% w/w to 40% w/w of Formula (I).

In a still further aspect, the direct compression formulation comprises between 15% w/w to 25% w/w of Formula (I).

In another aspect of the invention the direct compression formulation comprises about 20% w/w of Formula (I).

In a specific aspect of the invention, the direct compression formulation contains 21.33%±5% w/w of Formula (I).

In a further aspect, the direct compression formulation contains 20.26% w/w to 22.40% w/w of Formula (I).

In a still further aspect of the invention, the direct compression formulation comprises from 1% w/w to 50% w/w of an alkaline effervescent excipient.

In a further aspect, the direct compression formulation comprises from 1% w/w to 40% w/w of an alkaline effervescent excipient In a still further aspect, the direct compression formulation comprises from 10% to 30% w/w of an alkaline effervescent excipient.

In a still further aspect, the direct compression formulation comprises from 15% to 25% w/w of an alkaline effervescent excipient.

In a still further aspect, the direct compression formulation comprises about 20% w/w of an alkaline effervescent excipient.

In a further aspect of the invention, there is provided a direct compression formulation comprising from 10% w/w to 50% w/w of Formula (I) and from 1% w/w to 50% w/w of an effervescent agent; and further comprising one or more pharmaceutically acceptable ingredients.

In a further aspect of the invention, there is provided a direct compression formulation comprising from 15% w/w to 45% w/w of Formula (I) and from 10% w/w to 40% w/w of an effervescent agent; and further comprising one or more pharmaceutically acceptable ingredients.

In a further aspect of the invention, there is provided a direct compression formulation comprising from 15% w/w to 25% w/w of Formula (I) and from 15% w/w to 25% w/w of an effervescent agent; and further comprising one or more pharmaceutically acceptable ingredients.

The pharmaceutical composition and/or tablet and/or wet granulation formulation and/or roller compaction formulation and/or direct compression formulation can additionally and optionally include a colourant, as long as it is approved and certified by the FDA. For example, exemplary colours include allura red, acid fuschin D, napthalone red B, food orange 8, eosin Y, phyloxine B, erythrosine, natural red 4, carmine, red iron oxide, yellow iron oxide, black iron oxide, titanium dioxide and the like.

Sweetening agents can also be added to the pharmaceutical composition and/or tablet and/or wet granulation formulation and/or roller compaction formulation and/or direct compression formulation or to the the outer core of the tablet to create or add to the sweetness. Saccharide fillers and binders, e.g. mannitol, lactose, and the like, can add to this effect. For example, cyclamates, saccharin, aspartame, acesulfame K (Mukherjee (1997) Food Chem. Toxicol. 35:1177-1179), or the like (Rolls (1991) Am. J. Clin. Nutr. 53:872-878), can be used. Sweeteners other than sugars have the advantage of reducing the bulk volume of the pharmaceutical composition and/or tablet (core tablet and/or coat) and/or wet granulation formulation and/or roller compaction formulation and/or direct compression formulation and not effecting the physical properties of the tablet.

The pharmaceutical composition and/or tablet and/or wet granulation formulation and/or roller compaction formulation and/or direct compression formulation can additionally and optionally be coated using a conventional pan coater. The film coat may be applied by spraying an aqueous suspension of the coating ingredients onto the tablet cores.

Definitions

As used herein, the term "effervescent excipient" refers to any pharmaceutically acceptable material which evolves a gas in response to a stimulus, for example the evolution of carbon dioxide on acidification. An example of an effervescent excipient is a carbonate, for example a metal carbonate (such as sodium carbonate, potassium carbonate, magnesium carbonate, calcium carbonate or aluminium carbonate) or an organic carbonate (such as disodium glycine carbonate, dimethyl carbonate or ethylene carbonate). A further example of an effervescent excipient is a bicarbonate, for example a metal bicarbonate (such as sodium hydrogen carbonate or potassium hydrogen carbonate).

As used herein, the term "alkaline" refers to a material which induces an increase in pH when added to an aqueous system. The term "alkaline excipient" refers to any pharmaceutically acceptable material which is alkaline, for example an inorganic base such as disodium hydrogen phosphate or sodium hydroxide.

An alkaline effervescent excipient is a pharmaceutically acceptable material having both effervescent activity and alkaline properties, for example sodium hydrogen carbonate, potassium hydrogen carbonate, magnesium carbonate and sodium carbonate. For the avoidance of doubt, each of the alkaline effervescent excipients referred to above represents a separate and independent aspect of the invention. In one particular aspect of the invention, the alkaline effervescent excipient is selected from a metal carbonate or a metal bicarbonate. In another particular aspect of the invention, the alkaline effervescent excipient is selected from magnesium carbonate, sodium hydrogen carbonate, potassium hydrogen carbonate, or sodium carbonate. In a further particular aspect of the invention, the alkaline effervescent excipient is magnesium carbonate.

As used herein, the term "binding agent" refers to a pharmaceutically acceptable compound or composition added to a formulation to hold the active pharmaceutical ingredient and inactive ingredients together in a cohesive mix. Dry binders used for direct compaction must exhibit cohesive and adhesive forces so that when compacted the particles agglomerate. Binders used for wet granulation are hydrophilic and soluble in water and are usually dissolved in water to form a wet mass that is then granulated. Examples of suitable binding agents includes, but are not limited to, Povidone, Plasdone K29/32, Plasdone S-630, hydropropyl cellulose, methylcellulose, polyvinylpyrrolidone, aluminium stearate, hydroxypropylmethylcellulose and the like. It is possible for such binding agents to additionally act as water sequestering agents (e.g. Povidone).

As used herein, the term "filler" refers to any pharmaceutically acceptable material or composition added to a formulation to add bulk. Suitable fillers include, but are not limited to, mannitol, lactose, microcrystalline cellulose, silified microcrystalline cellulose and dicalcium phosphate.

As used herein, the term "lubricant" refers to any pharmaceutically acceptable agent which reduces surface friction, lubricates the surface of the granule, decreases tendency to build-up of static electricity, and/or reduces friability of the granules. Thus, lubricants can serve as anti-agglomeration agents. Conventional lubricants include stearic acid and related compounds such as magnesium stearate and sodium stearyl fumarate. Alternative lubricants include glyceryl dibehenate, colloidal silica, talc, other hydrogenated vegetable oil or triglycerides. Examples of suitable alternative lubricants include, but are not limited to, glyceryl dibehenate.

As used herein, the term "disintegrant" refers to materials added to the composition to help it break apart (disintegrate) and release the medicaments. Examples of disintegrants include, but are not limited to, non-saccharide water soluble polymers, such as cross-linked povidine. Other disintegrants that can also be used include, e.g. croscarmellose sodium, sodium starch glycolate, and the like, e.g. see Khattab (1992) J. Pharm. Pharmacol. 45:687-691.

The term "drying" and "dried" refer to a process which decreases the water content of a composition to a desired level.

The terms "compressing", "molding" and "pressing" refer to the process of applying compressive force to a formulation (powder or granules), as within a die, to form a tablet. The terms "compressed tablet" and "pressed tablet" mean any tablet formed by such a process.

The term "filming" refers to the adhesion of material to tablet punch surfaces. If sufficient material is allowed to build on punch surfaces then, among other defects, tablet weights may reduce below acceptable limits. (Journal of Pharmaceutical Sciences, Vol. 93(2), 2004).

The term "tablet" is used in its common context, and refers to a solid composition made by compressing and/or molding a mixture of compositions in a form convenient for swallowing or application to any body cavity.

As used herein, "tablet strength" is calculated based upon the amount of Compound I.

As used herein, "percent loading" is calculated by reference to the percentage by weight of Compound I The term "low pH" refers to a measured pH of less than 5, such as less than 3, for example between 0 and 3.

The term "satisfactory in vitro dissolution" refers to a percent dissolution of greater than or equal to 70% within 30 minutes in a suitable dissolution medium at 37° C.±0.5° C. as measured using the general procedure of the United States Pharmacopeia (Apparatus 2).

The term "stable formulation" refers to a formulation which, following storage for 4 weeks at elevated temperature and humidity, such as 40° C. and 75% relative humidity, exhibits water absorption of less than 10%, such as less than 5%, for example between 0 and 5%; and/or chemical degradation of less than 3%, such as less than 2.5%, for example between 0 and 2.5%; and/or which exhibits satisfactory in vitro dissolution.

The term "manufacturability" means the extent to which a product can be manufactured with relative ease at minimum cost and maximum reliability.

EXAMPLES

Figure 1:
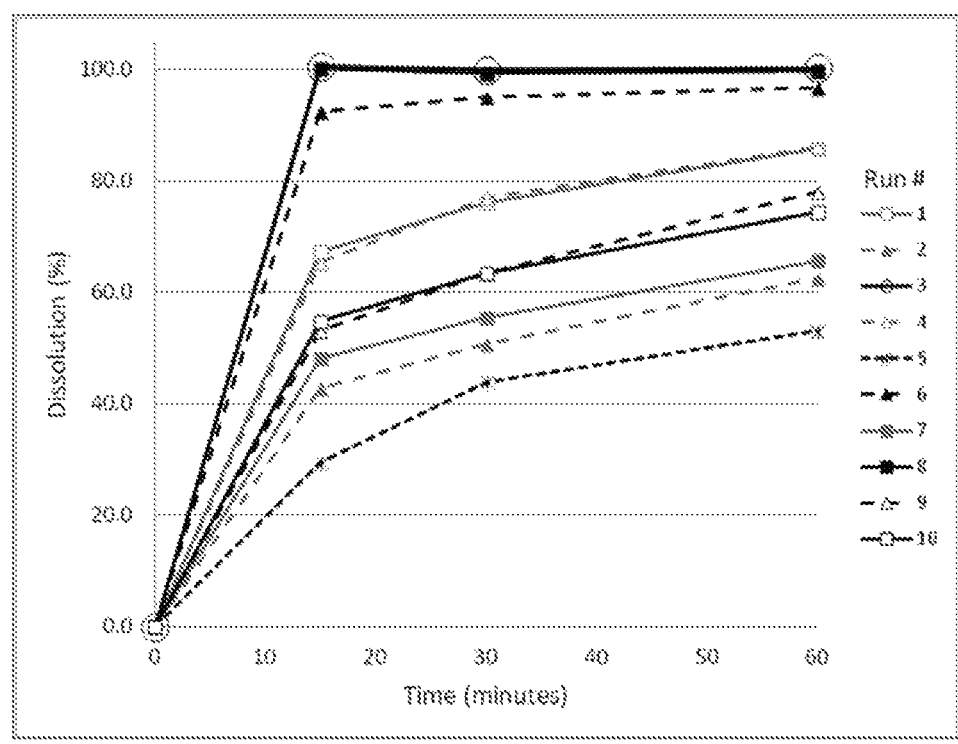
FIG. 1 shows a plot of the percentage dissolution using pH1.3 hydrochloric acid/sodium chloride buffer of ten alternative tablet formulations.

The invention is further understood by reference to the following examples, which are intended to be purely exemplary of the invention. The present invention is not limited in scope by the exemplified aspects, which are intended as illustrations of single aspects of the invention only. Various modifications of the invention in addition to those described herein will become apparent to those skilled in the art from the foregoing description and accompanying figures. Such modifications fell within the scope of the appended claims.

In the examples below as well as throughout the application, the following abbreviations have the following meanings. If not defined, the terms have their generally accepted meanings.

API=ActiveI Pharmaceutical Ingredient
CCS=croscarmellose sodium
CrosPov=crospovidone
BP=British Pharmacopoeia 2012
DCPA=dicalcium Phosphate (anhydrous)
DCPD=dicalcium Phosphate (dihydrate)
Glydb=glyceryl dibehenate
HPC=hydroxypropylcellulose
L-HPC=hydroxypropylcellulose, low-substituted
LOD=loss on drying
Mag carb=magnesium carbonate
MCC=cellulose, microcristaline
MgSt=magnesium stearate
min=minute
ml=milliliter
nm=nanometer
JP=Japanese Pharmacopeia 15$^{th}$ Edition, English Version (Society of Japanese Pharmacopoeia) 2006
PhEur=European Pharmacopoeia 6$^{th}$ Edition (Directorate for the Quality of Medicines of the Council of Europe) 2009
rpm=revolutions per minute
SLS=sodium lauryl sulphate
SSF=sodium stearyl fumurate
SSG=sodium starch glycolate
USP/USP-NF=United States Pharmacopeia 31/National Formulary 26 (The United States Pharmacopeia Convention) 2008
UV=ultraviolet
w/w=weight for weight Table 1 below shows materials used, pharmacopeial status, grade and supplier.

TABLE 1

| Material | Pharmacopeia | Grade | Supplier |
| --- | --- | --- | --- |
| Mannitol | PhEur USP-NF JP | Pearlitol 160c | Roquette Freres S.A. (France) |
| Cellulose, microcrystalline | PhEur USP-NF JP | Avicel ® PH-101 | FMC Biopolymer (Ireland) |
| Salicified cellulose, microcrystalline | USP-NF | Prosolv ® 90 | Rettenmaier UK Ltd (UK) |
| Dicalcium phosphate (anhydrous) | PhEur BP JP USP | Calipharm A | Innophos (USA) |
| Dicalcium phosphate (dihydrate) | PhEur BP JP USP | Calipharm D | Innophos (USA) |
| Sodium bicarbonate | PhEur BP JP USP | N/A | Dr Paul Lohmann (Germany) |
| Calcium carbonate (heavy) | PhEur BP JP USP | N/A | Dr Paul Lohmann (Germany) |
| Magnesium carbonate (heavy) | PhEur BP JP USP | N/A | Dr Paul Lohmann (Germany) |
| Disodium phosphate (dibasic) | PhEur BP JP USP-NF | N/A | Budenheim (USA) |
| Sodium starch glycolate | Ph Eur USP-NF | Glycolys LV | Roquette Freres S.A. (France) |
| Hydroxypropylcellulose, low-substituted | JP USP-NF | L-HPC | Shin Etsu, (Japan) |
| Croscarmellose sodium | Ph Eur USP JP | Ac-di-Sol | FMC Biopolymer (Ireland) |
| Crospovidone | PhEur BP USP-NF | Polyplasdone XL | Ashland Speciality Ingredients, (UK) |

TABLE 1-continued

| Material | Pharmacopeia | Grade | Supplier |
|---|---|---|---|
| Hydroxypropyl-cellulose | PhEur BP USP-NF JP | Klucel EXF | Ashland Speciality Ingredients (UK) |
| Hydroxypropyl-methylcellulose (hypromellose) | PhEur BP USP-NF JP | Pharmacoat 603 | Shin Etsu, (Japan) |
| Sodium lauryl sulphate (Sodium dodecyl sulfate) | USP NF | N/A | Sigma Aldrich (UK) |
| Magnesium stearate | PhEur USP-NF JP | NF Non Bovine | Mallinckrodt (USA) |
| Sodium stearyl fumarate | PhEur BP USP-NF | Pruv | JRS Pharma, (Germany) |
| Glyceryl dibehenate | PhEur USP | Compritol 888 ATO | Gattefosse (France) |
| Opadry II Biege | N/A | N/A | Colorcon (USA) |

Table 2 below shows equipment used, model and supplier.

TABLE 2

| Make | Model | Supplier |
|---|---|---|
| Pro-C-ept | Mi-pro | Pro-C-ept, Belgium |
| Diosna | P1/6 | Dierks & Söhne Gmbh, Osnabrück, Germany |
| Collette | Gral 10 & Gral 25 | Collette Machines, Belgium |
| Quadro | Comil U3 & Comil 194 | Quadro Engineering, Waterloo, Canada |
| WAB | Turbula T2F | Willy A. Bachofen AG, Muttenz, Switzerland |
| Copley Mobile Blender | Mobile Blender | Copley Scientific, Nottingham, UK |
| Aeromatic | Strea 1 | Casburt Pharmaceutical Equipment, Stoke-on-Trent, UK |
| Aeromatic-Fielder | MP1 | Aeromatic Fielder, Eastleigh, UK |
| Vector | MFL.01 | Vector Corporation, Marion, IA, U.S.A |
| Glatt | 59P | Glatt GmbH, Binzen, Germany |
| Riva | Piccola-Nova, | RivaSA, Buenos Aires, Argentina |
| Manesty | F3 | Manesty, Knowsley, UK |
| Korsch | Korsch XL100 | Korsch AG, Berlin, Germany |
| Riva | Riva mini-press | RivaSA, Buenos Aires, Argentina |
| Riva | Piccola W.I.P | RivaSA, Buenos Aires, Argentina |
| O'Hara | Labcoat II-X | O'hara technologies inc, Ontario, Canada |

Example 1: Assessment of Dissolution Performance of Ten Alternative Tablet Forms It has been found that the rheology of Formula (I) can change under certain conditions. In particular, Formula (I) can convert from a crystalline powder to a highly viscous material under low pH and at high concentration (both conditions need to be met simultaneously). Theoretically, these conditions will be met in the microenvironment of the tablet matrix either using a low pH dissolution method (e.g. pH1.3) or in the stomach. The relative surface area of Formula (I) reduces when the viscous material forms and this is associated with a reduced rate of solubilisation of Formula (I). This can be observed as a reduced rate of dissolution using a low pH method.

Based on this fundamental understanding, there are two hypothetical mechanisms to avoid the rheoligial transformation; first, to not allow Formula (I) to solubilise in a low pH environment (Hypothesis I); second, if dispersion in a low pH environment cannot be avoided, to disperse Formula (I) rapidly before the transformation can occur (Hypothesis II). Hypothesis II is dependent on the concentration of Formula (I) in the tablet matrix as higher concentrations of Formula (I) reduce the likelihood of rapid dispersion. Ten different prototype tablets were prepared from a wet granulation formulation using methods well known to those skilled in the art. The composition of each of these tablets is set out in Table 3.

TABLE 3

| Run | Formula (I), % w/w | MCC type (level, % w/w) | Mannitol level (% w/w) | pH Buffer type (% w/w) | Disintegrant Type (% w/w) | HPC (% w/w) |
|---|---|---|---|---|---|---|
| 1 | 20 | Avicel PH101 (48.5) | 20 | N/A | SSG (7.5) | 3 |
| 2 | 40 | Avicel PH101 (34.3) | 14.2 | N/A | SSG (7.5) | 3 |
| 3 | 40 | Avicel PH101 (16.7) | 11.8 | NaHCO$_3$ (20.0) | SSG (7.5) | 3 |
| 4 | 40 | Avicel PH101 (16.7) | 11.8 | CaCO$_3$ (20.0) | SSG (7.5) | 3 |
| 5 | 40 | Avicel PH101 (16.7) | 11.8 | Na$_2$HPO$_4$ (20.0) | SSG (7.5) | 3 |
| 6 | 40 | Avicel PH101 (16.7) | 11.8 | MgCO$_3$ (20.0) | SSG (7.5) | 3 |
| 7 | 40 | Prosolv ® SMCC (34.3) | 14.2 | N/A | SSG (7.5) | 3 |
| 8 | 40 | N/A | 31.0 | NaHCO$_3$ (20.0) | SSG (5) | 3 |
| 9 | 20 | Avicel PH101 (48.5) | 20 | N/A | CCS (7.5) | 3 |
| 10 | 20 | Avicel PH101 (48.5) | 20 | N/A | CrosPov (7.5) | 3 |

Run 1 is comparable to the Phase 1 clinical formulation and is the positive control. Run 2 is a negative control as it contains a high concentration of Formula (1) and has no alkalising agent. Run 5 tests Hypothesis I ($Na_2HPO_4$ is an alkalising agent). Runs 7, 9 and 10 test Hypothesis II (no alkalising agent, but varying disintegrants). Runs 3, 4, 6 and 8 test both Hypotheses I and II (they contain carbonate/bicarbonate alkalizing agents which both increase the pH microenvironment and liberate carbon dioxide in acidic conditions; carbon dioxide liberation can help to disperse Formula (I)).

Formula (I) and the excipients (except lubricant) described in Table 1 (total batch size approximately 250 g) were charged to a mixer-granulator (Diosna, 1 liter bowl, P1/6) and mixed. Purified water was added to the powders with further mixing until a suitable wet mass was formed. The resultant granules were dried to appropriate moisture content (≤2% w/w LOD) using a fluid bed dryer (Vector, MFL.01) with an inlet air temperature of 65° C. The dried granules were milled using an appropriately sized screen (1 mm, Quadro Comil U3).

SSF was then added to the granules (Table 4), which were then blended (WAB turbula) for 10 mins at 55 rpm before compressing into tablet cores using conventional tabletting equipment (Manesty F3 tablet press) Table 4

| Milled granules from composition variant (Table 1) | SSF Addition (% w/w) |
|---|---|
| 1 | 1 |
| 2 | 1 |
| 3 | 2 |
| 4 | 2 |
| 5 | 2 |
| 6 | 2 |
| 7 | 2 |
| 8 | 2 |
| 9 | 2 |
| 10 | 2 |

Concentration of SSF in the compositions was increased after Run 2 to allow viable processability during compression. Theoretically, this would reduce adhesion of material to tablet punches and dies (Pharmaceutical Powder Compaction Technology, edited by Goran Alderborn and Christer Nystrdm, Informa Healthcare, New York, 2008). However, increasing level of lubricant also typically reduces rate of dissolution due to the hydrophobic nature of the lubricant.

Further process conditions are given in Table 5.

TABLE 5

| Run | Chopper (rpm) | Impellor (rpm) | Total Water Added (ml) | Total granulation time (min) |
|---|---|---|---|---|
| 1 | 1000 | 300 | 81 | 4.1 |
| 2 | 1000 | 300 | 40 | 2.0 |
| 3 | 1500 | 750 | 65 | 6.5 |
| 4 | 1500 | 750 | 80 | 8.0 |
| 5 | 1500 | 750 | 80 | 8.0 |
| 6 | 1500 | 750 | 65 | 6.5 |
| 7 | 1500 | 750 | 70 | 7.0 |
| 8 | 1500 | 750 | 25 | 2.5 |
| 9 | 1500 | 750 | 80 | 8.0 |
| 10 | 1500 | 750 | 70 | 7.0 |

Impellor and chopper speeds were increased after Run 2 to allow viable processability during compression. Theoretically, increasing these process conditions increases granule density (Powder Technology, 117, pp 3-39, 2001) which aids granule flow and reduces punch filming. However, increasing granule density also typically reduces rate of dissolution.

Similarly, increasing total water added (Powder Technology, 88, pp 15-20, 1996) and granulation time (granule densification is a rate process) are also likely to increase granule density and thus reduce dissolution rate.

Dissolution was determined according to the general procedure of the United States Pharmacopeia using Apparatus 2 with pH1.3 hydrochloric acid and sodium chloride buffered solution at 37° C.±0.5° C. and stirrer speed of 50 rpm. At 15, 30 and 60 minutes dissolution media was withdrawn and the concentration of Formula (I) in solution was determined by UV spectroscopy at a wavelength of 311 nm against an external standard solution. Dissolution profiles are shown in FIG. 1, the dissolution data is presented in Table 6.

TABLE 6

| Run | 15 minutes | 30 minutes | 60 minutes |
|---|---|---|---|
| 1 | 67.4 | 76.1 | 85.8 |
| 2 | 42.9 | 50.7 | 62.6 |
| 3 | 100.6 | 99.9 | 100.3 |
| 4 | 65.3 | 77.0 | 86.1 |
| 5 | 29.4 | 43.8 | 53.1 |
| 6 | 92.4 | 95.1 | 96.7 |
| 7 | 48.1 | 55.5 | 65.7 |
| 8 | 100.1 | 99.3 | 99.7 |
| 9 | 53.2 | 63.4 | 78.0 |
| 10 | 54.9 | 63.4 | 74.4 |

Example 2: Assessment of Tablet Punch Filming of Ten Alternative Tablet Forms

Ten different prototype tablets were prepared from a wet granulation formulation using methods well known to those skilled in the art. The composition and manufacturing process of each of these tablets is described in Example 1.

Material adhesion to tablet punch surfaces (described below as 'filming') is a well known tabletting process defect (Journal of Pharmaceutical Sciences, Vol. 93(2), 2004). Extent of filming was visually assessed for each formulation and reported in Table 7.

TABLE 7

| Run | Filming |
|---|---|
| 1 | ★★ |
| 2 | ★★★ |
| 3 | ★ |
| 4 | No filming |
| 5 | No filming |
| 6 | ★ |
| 7 | ★★ |
| 8 | ★★★ |
| 9 | No filming |
| 10 | No filming |

★ = minor
★★ = moderate
★★★ = severe

Example 3: Assessment of Tablet Water Absorption of Ten Alternative Tablet Forms Ten different prototype tablets were prepared from a wet granulation formulation using methods well known to those skilled in the art. The composition and manufacturing process of each of these tablet compositions is described in Example 1.

Extent of water absorption was measured for each formulation (see Table 8). The tablets were exposed to a controlled environment (40° C. and 75% relative humidity) for one month.

TABLE 8

| Run | Water Absorption (% w/w) |
|---|---|
| 1 | 8.5 |
| 2 | 7.9 |
| 3 | 32.2 |
| 4 | 13.5 |
| 5 | 27.9 |
| 6 | 4.4 |
| 7 | 7.6 |
| 8 | 32.2 |
| 9 | 9.1 |
| 10 | 8.8 |

Example 4: Assessment of Dissolution Performance of a Further Nineteen Alternative Tablet Forms Run 6 (Examples 1, 2 and 3) was selected for further development because, unlike other compositions, it showed a marked improvement in pH1.3 dissolution (FIG. 1), an improvement in punch filming (Table 7) and low water absorption (Table 8).

A further nineteen different prototype tablets were prepared from a wet granulation formulation using methods well known to those skilled in the art. The composition of each of these tablets is qualitatively similar to Run 6. Quantitative compositions are set out in Table 9.

TABLE 9

| Run | Formula (I) (% w/w) | MCC (% w/w) | Mannitol (% w/w) | Mag Carb (% w/w) | HPC (% w/w) | SSG (% w/w) | SSF (% w/w) | Water Addition (% w/w) |
|---|---|---|---|---|---|---|---|---|
| 1 | 21.3 | 0.0 | 59.7 | 10.0 | 1.0 | 5.0 | 3.0 | 20.10 |
| 2 | 21.3 | 30.0 | 29.7 | 10.0 | 1.0 | 5.0 | 3.0 | 26.20 |
| 3 | 21.3 | 0.0 | 39.7 | 30.0 | 1.0 | 5.0 | 3.0 | 15.00 |
| 4 | 21.3 | 34.8 | 0.0 | 34.8 | 1.0 | 5.0 | 3.0 | 45.00 |
| 5 | 21.3 | 0.0 | 57.7 | 10.0 | 3.0 | 5.0 | 3.0 | 20.00 |
| 6 | 21.3 | 30.0 | 27.7 | 10.0 | 3.0 | 5.0 | 3.0 | 35.00 |
| 7 | 21.3 | 0.0 | 37.7 | 30.0 | 3.0 | 5.0 | 3.0 | 15.00 |
| 8 | 21.3 | 33.8 | 0.0 | 33.8 | 3.0 | 5.0 | 3.0 | 40.20 |
| 9 | 21.3 | 0.0 | 54.7 | 10.0 | 1.0 | 10.0 | 3.0 | 20.00 |
| 10 | 21.3 | 30.0 | 24.7 | 10.0 | 1.0 | 10.0 | 3.0 | 30.00 |
| 11 | 21.3 | 0.0 | 34.7 | 30.0 | 1.0 | 10.0 | 3.0 | 30.40 |
| 12 | 21.3 | 32.3 | 0.0 | 32.3 | 1.0 | 10.0 | 3.0 | 40.00 |
| 13 | 21.3 | 0.0 | 52.7 | 10.0 | 3.0 | 10.0 | 3.0 | 20.30 |
| 14 | 21.3 | 30.0 | 22.7 | 10.0 | 3.0 | 10.0 | 3.0 | 32.50 |
| 15 | 21.3 | 0.0 | 32.7 | 30.0 | 3.0 | 10.0 | 3.0 | 32.40 |
| 16 | 21.3 | 31.3 | 0.0 | 31.3 | 3.0 | 10.0 | 3.0 | 35.30 |
| 17 | 21.3 | 15.0 | 31.2 | 20.0 | 2.0 | 7.5 | 3.0 | 40.00 |
| 18 | 21.3 | 15.0 | 31.2 | 20.0 | 2.0 | 7.5 | 3.0 | 40.00 |
| 19 | 21.3 | 15.0 | 31.2 | 20.0 | 2.0 | 7.5 | 3.0 | 40.30 |

Formula (I) and the excipients described in Table 9 (total batch size approximately 1.5 kg) were charged to a mixer-granulator (Colette Gral 10) and mixed. Purified water (Ranging from 15% w/w to 45% w/w as set out in Table 9) was added to the powders with further mixing until a suitable wet mass was formed (ranging from approximately 3 to 14 mins) at 420 rpm. The resultant granules were dried to appropriate moisture content (≤2% LOD) using a fluid bed dryer (Aeromatic Strea 1) with an inlet air temperature of 80° C. The dried granules were milled using an appropriately sized screen (1.4 mm, Quadro Comil U3). SSF was then added to the granules, which were then blended (Copley, Mobile Blender 7.5 liter drum) for 5 mins at 25 rpm before compressing into tablet cores using conventional tabletting equipment (Korch XL 100).

Figure 2:
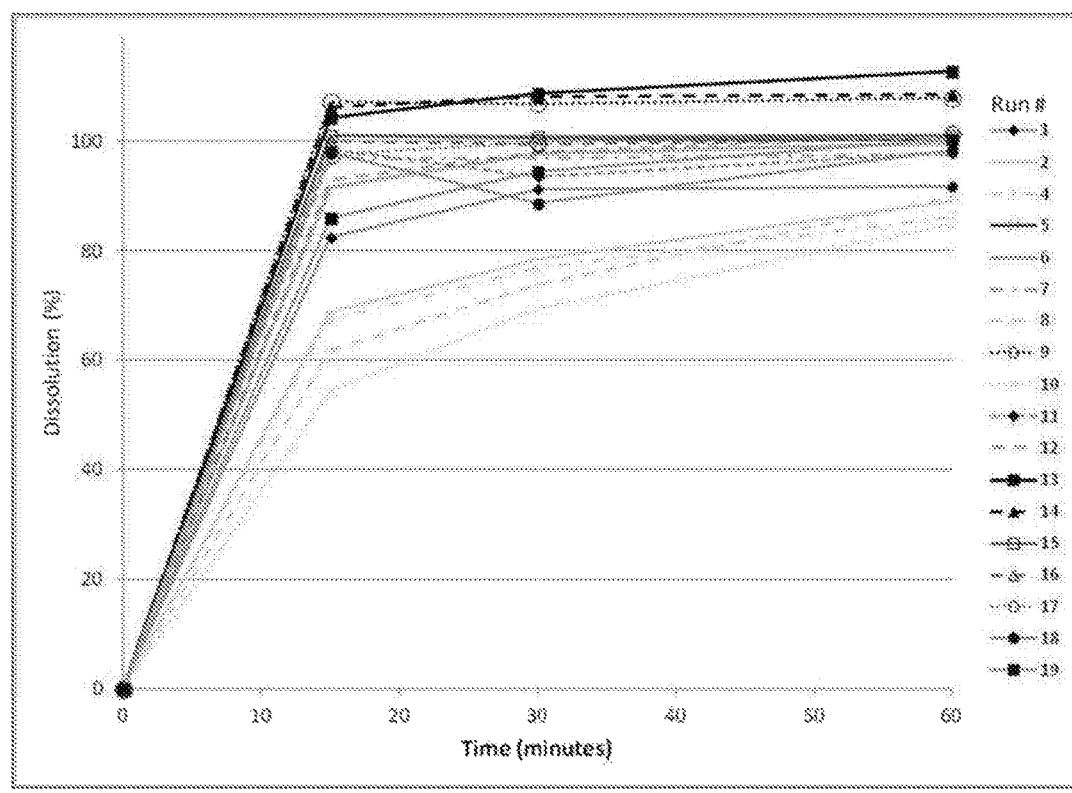
FIG. 2 shows a plot of the percentage dissolution using pH1.3 hydrochloric acid/sodium chloride buffer of a further nineteen alternative tablet formulations.

Dissolution was determined according to the general procedure of the United States Pharmacopeia using Apparatus 2 with pH1.3 hydrochloric acid and sodium chloride buffered solution at 37° C.±0.5° C. and stirrer speed of 50 rpm. At 15, 30 and 60 minutes dissolution media was withdrawn and the concentration of Formula (I) in solution was determined by UV spectroscopy at a wavelength of 311 nm against an external standard solution. Dissolution profiles are shown in FIG. 2, the dissolution data is presented in Table 10.

TABLE 10

| Run | 15 minutes | 30 minutes | 60 minutes |
|---|---|---|---|
| 1 | 82.6 | 91.3 | 91.8 |
| 2 | 68.9 | 78.6 | 89.2 |
| 4 | 67.5 | 77 | 86.3 |
| 5 | 101.1 | 100.7 | 100.2 |
| 6 | 91.7 | 97.8 | 99.8 |
| 7 | 96.9 | 97 | 97.5 |
| 8 | 61.8 | 73.9 | 89.9 |
| 9 | 107.2 | 106.9 | 107.9 |
| 10 | 54.5 | 69.4 | 84.9 |
| 11 | 98.6 | 93.6 | 98 |
| 12 | 92.9 | 97.9 | 101.3 |
| 13 | 104.3 | 108.7 | 112.8 |
| 14 | 106.3 | 108.1 | 108.5 |
| 15 | 101.1 | 100.8 | 101.1 |
| 16 | 100 | 99.5 | 100.4 |
| 17 | 97.5 | 99.9 | 101.3 |

TABLE 10-continued

| Run | 15 minutes | 30 minutes | 60 minutes |
|---|---|---|---|
| 18 | 97.9 | 88.7 | 98.3 |
| 19 | 86 | 94.5 | 100.4 |

Example 5: Assessment of Chemical Stability of a Sixteen Alternative Tablet Forms Sixteen different prototype tablets were prepared from a wet granulation formulation using methods well known to those skilled in the art. The composition and manufacturing process of each of these tablets is described in Table 11.

TABLE 11

| Run Order | Main Filler | Secondary Filler | Disintegrant | Binder | Surfactant | Lubricant |
|---|---|---|---|---|---|---|
| 1 | Mannitol | DCPA | L-HPC | HPC | None | SSF |
| 2 | Mannitol | DCPD | SSG | HPC | None | SSF |
| 3 | Mannitol | DCPD | L-HPC | HPC | SLS | MgST |
| 4 | Mannitol | DCPA | SSG | HPMC | SLS | SSF |
| 5 | Mannitol | DCPA | L-HPC | HPMC | None | MgST |
| 6 | MCC | DCPA | SSG | HPMC | None | SSF |
| 7 | MCC | DCPA | L-HPC | HPC | SLS | SSF |
| 8 | Mannitol | DCPD | L-HPC | HPMC | SLS | SSF |
| 9 | MCC | DCPD | L-HPC | HPMC | None | SSF |
| 10 | MCC | DCPA | L-HPC | HPMC | SLS | MgST |
| 11 | MCC | DCPA | SSG | HPC | None | MgST |
| 12 | MCC | DCPD | L-HPC | HPC | None | MgST |
| 13 | Mannitol | DCPA | SSG | HPC | SLS | MgST |
| 14 | Mannitol | DCPD | SSG | HPMC | None | MgST |
| 15 | MCC | DCPD | SSG | HPMC | SLS | MgST |
| 16 | MCC | DCPD | SSG | HPC | SLS | SSF |

Formula (I) and the excipients (except lubricant) described in Table 11 (total batch size approximately 50 g) were charged to a mixer-granulator (Mi-Pro, 500 ml bowl) and mixed. Purified water was added (approximately 10 ml/min) to the powders with further mixing until a suitable wet mass was formed. The resultant granules were dried to appropriate moisture content (≤2% w/w LOD) using a fluid bed dryer (Vector, MF1.01). The dried granules were milled using an appropriately sized screen (1 mm, Quadro Comil U3). Lubricant was then added to the granules, which were then blended (WAB turbula) for 4 mins at 24 rpm before compressing into tablet cores using conventional tab letting equipment (Manesty F3 tablet press).

Total impurities were measured by injection of the prepared sample and standard solutions onto an LC system selected to ensure the separation of Formula (I) from organic impurities and excipients. The chromatographic responses due to Formula (I) and organic impurities are measured on a UV detector at wavelength 245 nm. The response due to Formula (I) present in the sample was compared to that of a standard and its assay was calculated. The level of organic impurities was calculated as % w/w. Equivalent response was assumed between Formula (I) and organic impurities, Samples were stored in a controlled environment for four weeks at 60° C. and 80% relative humidity. After analysis, samples with SSF in their composition contained 0.99±0.36% (mean±standard deviation %) and samples with MgSt in their composition contained 1.93±1.34% (mean±standard deviation %).

Example 6: Assessment of Dissolution Performance when Varying SSF Concentration and Inclusion of an Alternative Lubricant Full extent of release was not achieved for each of the prototype formulations presented in Example 4 in pH 6.8 phosphate buffered solution. The affect of lubricant was investigated and five different prototype tablets were prepared by a wet granulation process using methods well known to those skilled in the art. The composition of each of these tablets is described in Table 12.

TABLE 12

| Run | Milled granules from composition variant (Table 5) | SSF (% w/w) | Glydb (% w/w) |
|---|---|---|---|
| 0% SSF | 17 and 18 | 0.0 | N/A |
| 1% SSF | 17 and 18 | 1.0 | N/A |
| 2% SSF | 17 and 18 | 2.0 | N/A |
| 5% SSF | 17 and 18 | 5.0 | N/A |
| 3% Glybd | 17 and 18 | N/A | 3.0 |

Figure 3:
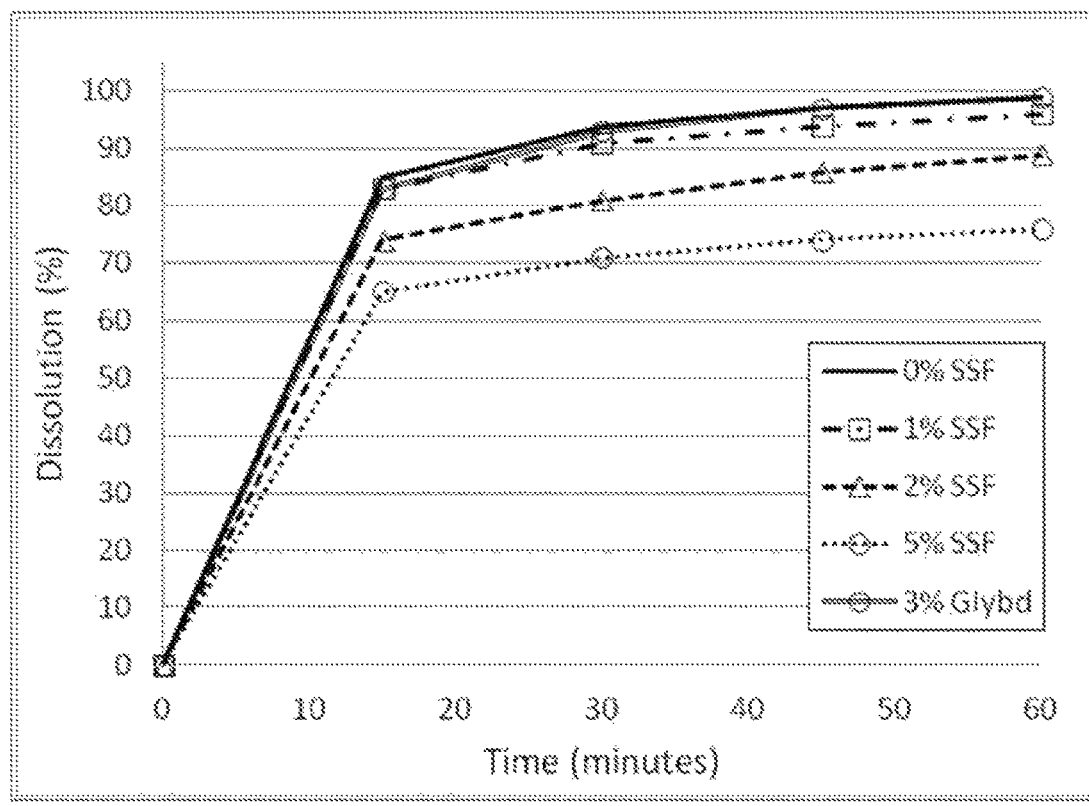
FIG. 3 shows a plot of the percentage dissolution using pH6.8 phosphate buffer of five alternative tablet formulations in which the lubricant content was varied.

Milled unlubricated granules from the prototype variants 17 and 18 (equivalent compositions), presented in example 4 (Table 9), were combined with the relevant level of lubricant, presented in Table 12, and blended (WAB turbula) for 5 mins at 25 rpm before compressing into tablet cores using conventional tabletting equipment (RIVA mini-press). Dissolution was determined according to the general procedure of the United States Pharmacopeia using Apparatus 2 with pH6.8 phosphate buffered solution at 37° C.±0.5° C. and stirrer speed of 75 rpm. At 15, 30, 45 and 60 minutes dissolution media was withdrawn and the concentration of Formula (I) in solution was determined by UV spectroscopy at a wavelength of 298 nm against an external standard solution. Dissolution results are shown in FIG. 3 and the dissolution data is presented in Table 13.

TABLE 13

| Run | 15 minutes | 30 minutes | 45 minutes | 60 minutes |
|---|---|---|---|---|
| 0% SSF | 85 | 94 | 97 | 99 |
| 1% SSF | 83 | 91 | 94 | 96 |
| 2% SSF | 74 | 81 | 86 | 89 |
| 5% SSF | 65 | 71 | 74 | 76 |
| 3% Glybd | 83 | 93 | 97 | 99 |

Example 7: Assessment of Tablets of Formula (I) Prepared with Different Lubricants Three different prototype tablets were prepared from a wet granulation formulation using methods well known to those skilled in the art. The composition of each of these tablets (including a range of lubricants i.e. MgSt, SSF and Glydb) is described below. The pharmaceutical composition comprises the following components (% w/w):

| | Composition A (% w/w) | Composition B (% w/w) | Composition C (% w/w) |
|---|---|---|---|
| API | Formula (I) 10.0 | Formula (I) 21.3 | Formula (I) 21.3 |
| Primary Filler | Mannitol 60.0 | Mannitol 31.2 | Mannitol 31.2 |
| Secondary Filler | DCPD 20.0 | MCC 15.0 | MCC 15.0 |
| Tertiary Filler | | $MgCO_3$ 20.0 | $MgCO_3$ 20.0 |
| Disintegrant | SSG 5.0 | SSG 7.5 | SSG 7.5 |
| Binder | HPMC 4.0 | HPC 2.0 | HPC 2.0 |
| Lubricant | MgSt 1.0 | SSF 3.0 | Glydb 3.0 |

Manufacturing processes for Compositions A, B and C are given in Example 5, Example 4 and Example 6, respectively.

An evaluation of tablet dissolution performance was made (Table 14). Dissolution was determined according to the general procedure of the United States Pharmacopeia using Apparatus 2 with pH6.8 phosphate buffered solution at 37° C.±0.5° C. and stirrer speed of 50 rpm. At 15, 30, and 60 minutes dissolution media was withdrawn and the concentration of Formula (I) in solution was determined by UV spectroscopy at a wavelength of 298 nm against an external standard solution.

TABLE 14

| Composition | 15 minutes | 30 minutes | 60 minutes |
| --- | --- | --- | --- |
| A | 55.8 | 82.5 | 88.3 |
| B | 69.3 | 76.3 | 78.1 |
| C | 79.0 | 88.2 | 93.7 |

Composition C was selected for further study because, unlike other compositions, it (i) did not contain MgSt, which on average gave more impurities than SSF (Example 5); (ii) did not contain SSF, inclusion of which can affect extent of dissolution release (FIG. 3); and (iii), demonstrated acceptable dissolution performance throughout the physiologically relevant pH range (Table 15).

TABLE 15

| Composition C | 15 minutes | 30 minutes | 60 minutes |
| --- | --- | --- | --- |
| pH 1.3 | 98.2 | 101.5 | 102.0 |
| pH 6.8 | 79.0 | 88.2 | 93.7 |

Example 8: Assessment of Dissolution Performance of Ten Alternative Tablet Formulations Ten alternative prototype tablets were prepared from a wet granulation using methods well known to those skilled in the art. The composition of each of these tablets is qualitatively similar to Composition C (Example 7). Quantitative compositions are set out in Table 16.

TABLE 16

| Composition | API (% w/w) | MgCO3 (% w/w) | Glydb (% w/w) | Mannitol (% w/w) | MCC (% w/w) | SSG (% w/w) | HPC (% w/w) |
| --- | --- | --- | --- | --- | --- | --- | --- |
| 1 | 10 | 15 | 8 | 38.72 | 18.78 | 7.5 | 2 |
| 2 | 40 | 25 | 8 | 11.67 | 5.83 | 7.5 | 2 |
| 3 | 10 | 25 | 1 | 36.79 | 17.71 | 7.5 | 2 |
| 4 | 40 | 15 | 1 | 23.29 | 11.21 | 7.5 | 2 |
| 5 | 40 | 25 | 8 | 11.67 | 5.83 | 7.5 | 2 |
| 6 | 10 | 15 | 1 | 43.55 | 20.95 | 7.5 | 2 |
| 7 | 40 | 25 | 1 | 16.54 | 7.96 | 7.5 | 2 |
| 8 | 10 | 25 | 8 | 31.67 | 15.83 | 7.5 | 2 |
| 9 | 21.33 | 20 | 3 | 31.17 | 15 | 7.5 | 2 |
| 10 | 21.33 | 20 | 3 | 31.17 | 15 | 7.5 | 2 |

Formula (I) and the excipients (except lubricant) described in Table 16 (total batch size approximately 250 g) were charged to a mixer-granulator (Diosna, 1 liter bowl, P1/6) and mixed. Purified water was added (approximately 10 ml/min) to the powders with further mixing until a suitable wet mass was formed. The resultant granules were dried to appropriate moisture content (≤2% w/w LOD) using a fluid bed dryer (Aeromatic Strea 1). The dried granules were milled using an appropriately sized screen (1.4 mm, Quadro Comil U3). Lubricant was then added to the granules, which were then blended (WAB turbula) for 10 mins at 55 rpm. The granules were then compressed into tablet cores (each core normalised to 80 mg of formula 1) using conventional tabletting equipment (Riva Piccola (W.I.P) tablet press) at a normalised pressure of 100 MPa.

Figure 4:
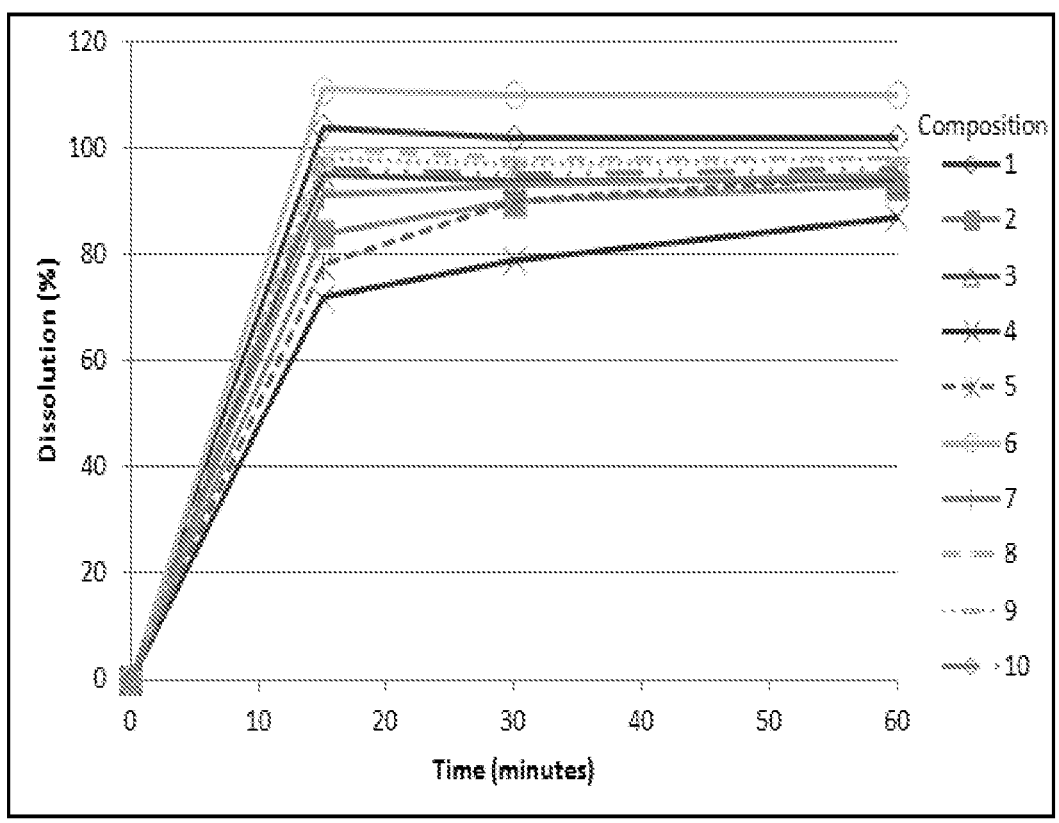
FIG. 4 shows a plot of the percentage dissolution using pH1.3 hydrochloric acid/sodium chloride buffer for ten alternative tablet formulations in which Formula (I), magnesium carbonate and lubricant was varied.
Figure 5:
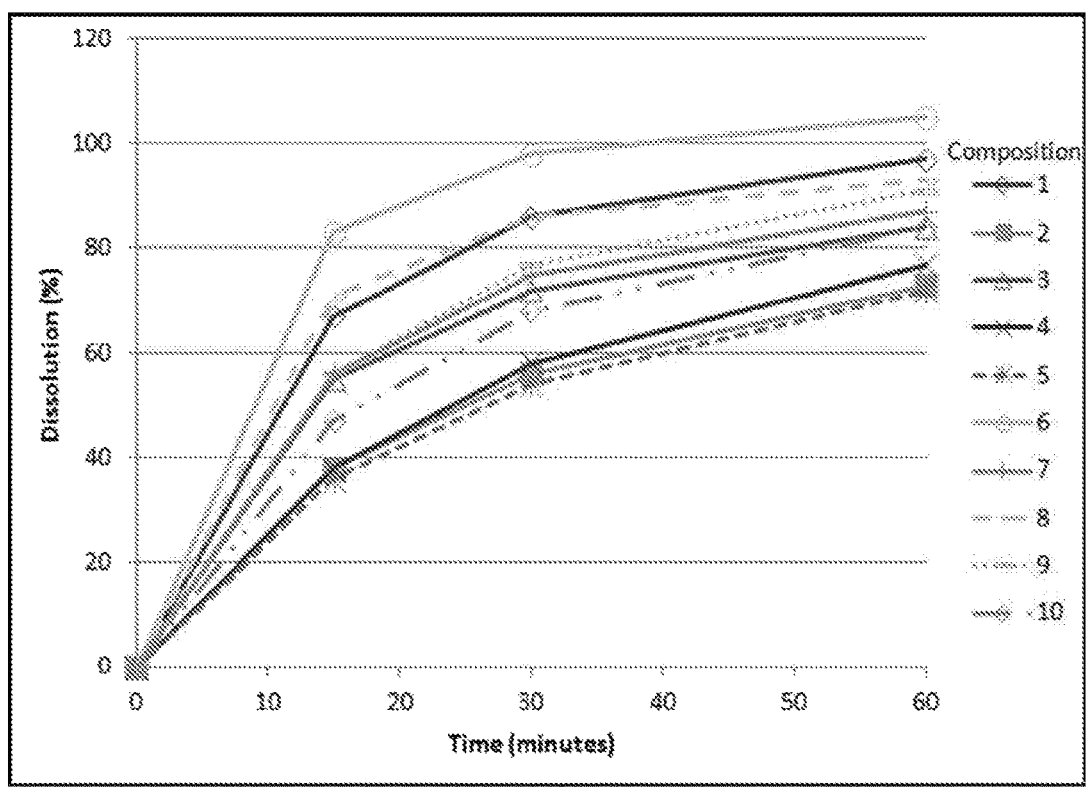
FIG. 5 shows a plot of the percentage dissolution using pH6.8 phosphate buffer for ten alternative tablet formulations in which Formula (I), magnesium carbonate and lubricant was varied.

An evaluation of tablet dissolution performance was made (Table 17 and 18). Dissolution was determined according to the general procedure of the United States Pharmacopeia using Apparatus 2 with both pH6.8 phosphate solution and pH1.3 hydrochloric acid and sodium chloride solution at 37° C.±0.5° C. and stirrer speed of 50 rpm. At 15, 30, and 60 minutes dissolution media was withdrawn and the concentration of Formula (I) in solution was determined by UV spectroscopy at a wavelength of 311 nm (for pH 1.3 solution) or 298 nm (for pH 6.8 solution) against an external standard solution. Dissolution results are shown in Table 17/FIG. 4 (pH 1.3) and Table 18/FIG. 5 (pH 6.8).

TABLE 17

| Composition | 15 minutes | 30 minutes | 60 minutes |
| --- | --- | --- | --- |
| 1 | 104 | 102 | 102 |
| 2 | 84 | 90 | 93 |
| 3 | 95 | 94 | 94 |
| 4 | 72 | 79 | 87 |
| 5 | 78 | 90 | 95 |
| 6 | 111 | 110 | 110 |
| 7 | 91 | 93 | 95 |
| 8 | 100 | 98 | 98 |
| 9 | 98 | 97 | 98 |
| 10 | 96 | 95 | 96 |

TABLE 18

| Composition | 15 minutes | 30 minutes | 60 minutes |
| --- | --- | --- | --- |
| 1 | 67 | 86 | 97 |
| 2 | 38 | 56 | 73 |
| 3 | 55 | 72 | 84 |
| 4 | 38 | 58 | 77 |
| 5 | 36 | 54 | 72 |

TABLE 18-continued

| Composition | 15 minutes | 30 minutes | 60 minutes |
| --- | --- | --- | --- |
| 6 | 83 | 98 | 105 |
| 7 | 56 | 75 | 87 |
| 8 | 71 | 86 | 93 |
| 9 | 56 | 77 | 91 |
| 10 | 47 | 68 | 84 |

Example 9: Assessment of Tablet Punch Filming Often Alternative Tablet Formulations Ten alternative prototype tablets were prepared from a wet granulation formulation using methods well known to those skilled in the art. The composition and manufacturing process of each of these tablets is described in Example 8.

Material adhesion to tablet punch surfaces (described below as 'filming') is a well known tabletting process defect (Journal of Pharmaceutical Sciences, Vol. 93(2), 2004). Extent of filming was visually assessed for each formulation and reported in Table 19.

TABLE 19

| Composition | Filming |
|---|---|
| 1 | No filming |
| 2 | No filming |
| 3 | ★★ |
| 4 | ★★ |
| 5 | No filming |
| 6 | ★★ |
| 7 | ★★★ |
| 8 | No filming |
| 9 | No filming |
| 10 | No filming |

★ = minor
★★ = moderate
★★★ = severe

No punch filming was observed for the compositions with 3-8% w/w glydb. Moderate to severe levels of punch filming was observed for the compositions containing 1% w/w glydb under the process conditions applied.

Example 11: Assessment of Dissolution of an Alternative Tablet Formulation

One alternative tablet formulation was prepared from a wet granulation using methods well known to those skilled in the art. The composition of the tablet core is quantitatively similar to Composition C (Example 7) and a film coat was applied using a conventional film coating method to enhance the tablet appearance. The quantitative composition of the tablet core formulation is presented in Table 20.

TABLE 20

| Component | Composition (% w/w) |
|---|---|
| AZD4547 | 21.33 |
| Mannitol | 31.17 |
| Micro crystaline cellulose (Avicel PH101) | 15 |
| Magnesium Carbonate (Heavy) | 20 |
| Sodium Starch Glycolate | 7.5 |
| Hydroxy Propyl Cellulose | 2 |
| Glyceryl dibehenate | 3 |

A film coat was applied using a propriety mixture of coating excipients, Opadry II Biege, supplied by Colorcon.

Formula (I) and the excipients (except lubricant) described in Table 20 (total batch size approximately 5 kg) were charged to a mixer-granulator (Gral 25) and mixed. Purified water was added (approximately 166 ml/min) to the powders with further mixing until a suitable wet mass was formed. The resultant granules were dried to appropriate moisture content (≤2% w/w LOD) using a fluid bed dryer (Glatt 59P). The dried granules were milled using an appropriately sized screen (1.4 mm, Quadro Comil U3). Lubricant was then added to the granules, which were then blended (Copley Mobile Blender, 7.5 L container) for 5 mins at 25 rpm. The granules were then compressed into tablet cores using conventional tabletting equipment (Riva Piccola-Nova, tablet press) to achieve a target compression weight of 375 mg. The tablet cores were over coated with a film coat using conventional pan coating equipment (O'Hara Labcoat II-X) to achieve a tablet weight gain of 3% w/w.

An evaluation of tablet dissolution performance was made (Table 22). Dissolution was determined according to the general procedure of the United States Pharmacopeia using Apparatus 2 with both pH6.8 phosphate solution and pH1.3 hydrochloric acid and sodium chloride solution at 37° C.±0.5° C. and stirrer speed of 50 rpm. At 15, 30 and 60 minutes dissolution media was withdrawn and the concentration of Formula (I) in solution was determined by UV spectroscopy at a wavelength of 311 nm (for pH 1.3 solution) or 298 nm (for pH 6.8 solution) against an external standard solution.

TABLE 22

| | 15 minutes | 30 minutes | 60 minutes |
|---|---|---|---|
| pH 1.3 | 95 | 101 | 103 |
| pH 6.8 | 75 | 87 | 93 |

The invention claimed is:

1. A pharmaceutical composition comprising 15% w/w to 25% w/w of the compound of Formula (I):

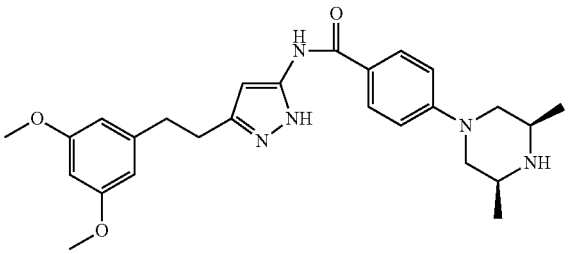

and 15% w/w to 25% w/w of an alkaline effervescent agent that is sufficient to provide satisfactory in vitro dissolution at a pH where the compound of Formula (I) is no more than slightly soluble, wherein the effervescent agent is magnesium carbonate; wherein the composition comprises between 0.25% w/w and 8% w/w of an alternative lubricant; wherein the alternative lubricant is glyceryl dibehenate; and further comprising one or more pharmaceutically acceptable ingredients.

2. A pharmaceutical composition according to claim 1 wherein the composition comprises between 2.5% w/w and 3.5% w/w of the alternative lubricant.

3. A pharmaceutical composition according to claim 1, wherein the in vitro dissolution is greater than or equal to 70% dissolution of the compound of Formula (I) within 30 minutes at pH 1.3.

4. A pharmaceutical composition comprising:
(a) 15% w/w to 25% w/w of a pharmaceutically active compound, wherein the pharmaceutically active compound consists of the compound of Formula (I):

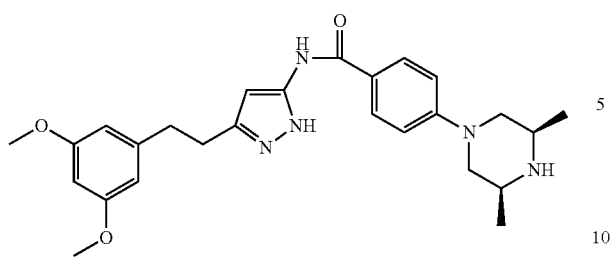

and
(b) 15% w/w to 25% w/w of an alkaline effervescent agent that is sufficient to provide satisfactory in vitro dissolution, wherein the effervescent agent is magnesium carbonate; wherein the composition comprises between 0.25% w/w and 8% w/w of an alternative lubricant; wherein the alternative lubricant is glyceryl dibehenate; and
(c) further comprising one or more pharmaceutically acceptable ingredients.

* * * * *